(12) United States Patent
Guerra et al.

(10) Patent No.: US 8,703,481 B2
(45) Date of Patent: Apr. 22, 2014

(54) EPISOMAL EXPRESSION VECTOR FOR METAZOAN CELLS

(76) Inventors: Cesar E. Guerra, Late of Guilford, CT (US); Michelle Dunham Guerra, legal representative, Guilford, CT (US); Harvey L. Ozer, Hoboken, NJ (US)

( * ) Notice: Subject to any disclaimer, the term of this patent is extended or adjusted under 35 U.S.C. 154(b) by 1162 days.

(21) Appl. No.: 12/306,234

(22) PCT Filed: Jun. 22, 2007

(86) PCT No.: PCT/US2007/071911
§ 371 (c)(1),
(2), (4) Date: Aug. 10, 2009

(87) PCT Pub. No.: WO2007/150036
PCT Pub. Date: Dec. 27, 2007

(65) Prior Publication Data
US 2012/0052529 A1    Mar. 1, 2012

Related U.S. Application Data

(60) Provisional application No. 60/815,724, filed on Jun. 22, 2006.

(51) Int. Cl.
*C12N 15/63* (2006.01)
*C12N 15/85* (2006.01)

(52) U.S. Cl.
USPC .................................. 435/320.1; 435/325

(58) Field of Classification Search
None
See application file for complete search history.

(56) References Cited

U.S. PATENT DOCUMENTS

2003/0033617 A1* 2/2003 Hadlaczky et al. ............... 800/6
2004/0209239 A1* 10/2004 Lieberman ....................... 435/5

OTHER PUBLICATIONS

Tolmachova et al. Analysis of a YAC with human telomeres and oriP from epstein-barr virus in yeast and 293 cells. Nucleic Acids Res. Sep. 15, 1999;27(18):3736-44.*
D'Aiuto et al., Generation of a Telomere-Based Episomal Vector. Biotechnol. Prog. 2003, vol. 19, pp. 1775-1780.

* cited by examiner

*Primary Examiner* — Michele K Joike
(74) *Attorney, Agent, or Firm* — Fox Rothschild LLP

(57) ABSTRACT

The invention relates to a vector comprising an origin of replication for episomal maintenance in a metazoan cell, a gene for episomal maintenance in the metazoan cell, and a telomeric polynucleotide sequence. The vector can be used for episomal expression of RNA and polypeptides in metazoan cells.

16 Claims, 14 Drawing Sheets

```
   1 TTGTTCCAGT TTGGAACAAG AGTCCACTAT TAAAGAACGT GGACTCCAAC
  51 GTCAAAGGGC GAAAAACCGT CTATCAGGGC GATGGCCCAC TACGTGAACC
 101 ATCACCCTAA TCAAGTTTTT TGGGGTCGAG GTGCCGTAAA GCACTAAATC
 151 GGAACCCTAA AGGGAGCCCC CGATTAGAG CTTGACGGGG AAAGCCGGCG
 201 AACGTGGCGA GAAAGGAAGG GAAGAAAGCG AAAGGAGCGG GCGCTAGGGC
 251 GCTGGCAAGT GTAGCGGTCA CGCTGCGCGT AACCACCACA CCCGCCGCGC
 301 TTAATGCGCC GCTACAGGGC GCGTCCCATT CGCCATTCAG GCTGCGCAAC
 351 TGTTGGGAAG GGCGATCGGT GCGGCCTCT TCGCTATTAC GCCAGCTGGC
 401 GAAAGGGGGA TGTGCTGCAA GGCGATTAAG TTGGGTAACG CCAGGGTTTT
 451 CCCAGTCACG ACGTTGTAAA ACGACGGCCA GTGAATTGTA ATACGACTCA
 501 CTATAGGGCG AATTGGGTAC CGGGCCCCCC CTCGAGGGGG GTTGGGGTTG
 551 GGGTTGGGGT TGGGGTTGGG GTTGGGGTTG GGGTTGGGGT TGGGGTTGGG
 601 GTTGGGGTTG GGGTTGGGGT TGGGGTTGGG GTTGGGGTTG GGGTTGGGGT
 651 TGGGGTCTGC CTCGCGCGGA TCCCGGGTAA TAACTGATAT AATTAAATTG
 701 AAGCTCTAAT TTGTGAGTTT AGTATACATG CATTTACTTA TAATACAGTT
 751 TTTTAGTTTT GCTGGCCGCA TCTTCTCAAA TATGCTTCCC AGCCTGCTTT
 801 TCTGTAACGT TCACCCTCTA CCTTAGCATC CCTTCCCTTT GCAAATAGTC
 851 CTCTTCCAAC AATAATAATG TCAGATCCTG TAGAGACCAC ATCATCCACG
 901 GTTCTATACT GTTGACCCAA TGCGTCTCCC TTGTCATCTA AACCCACACC
 951 GGGTGTCATA ATCAACCAAT CGTAACCTTC ATCTCTTCCA CCCATGTCTC
1001 TTTGAGCAAT AAAGCCGATA ACAAAATCTT TGTCGCTCTT CGCAATGTCA
1051 ACAGTACCCT TAGTATATTC TCCAGTAGAT AGGGAGCCCT TGCATGACAA
1101 TTCTGCTAAC ATCAAAGGC CTCTAGGTTC CTTTGTTACT TCTTCTGCCG
1151 CCTGCTTCAA ACCGCTAACA ATACCTGGGC CCACCACACC GTGTGCATTC
1201 GTAATGTCTG CCCATTCTGC TATTCTGTAT ACACCCGCAG AGTACTGCAA
1251 TTTGACTGTA TTACCAATGT CAGCAAATTT TCTGTCTTCG AAGAGTAAAA
1301 AATTGTACTT GGCGGATAAT GCCTTTAGCG GCTTAACTGT GCCCTCCATG
1351 GAAAAATCAG TCAAGATATC CACATGTGTT TTTAGTAAAC AAATTTTGGG
1401 ACCTAATGCT TCAACTAACT CCAGTAATTC CTTGGTGGTA CGAACATCCA
1451 ATGAAGCACA CAAGTTTGTT TGCTTTTCGT GCATGATATT AAATAGCTTG
1501 GCAGCAACAG GACTAGGATG AGTAGCAGCA CGTTCCTTAT ATGTAGCTTT
1551 CGACATGATT TATCTTCGTT TCCTGCAGGT TTTTGTTCTG TGCAGTTGGG
1601 TTAAGAATAC TGGGCAATTT CATGTTTCTT CAACACTACA TATGCGTATA
1651 TATACCAATC TAAGTCTGTG CTCCTTCCTT CGTTCTTCCT TCTGTTCGGA
1701 GATTACCGAA TCAAAAAAAT TTCAAGGAAA CCGAAATCAA AAAAAAGAAT
1751 AAAAAAAAAA TGATGAATTG AAAAGCTCCA TTCCTTGCGG CGGCGGTGCT
1801 CAACGGCCTC AACCTACTAC TGGGCTGCTT CCTAATGCAG GAGTCGCATA
1851 AGGGAGAGCG TCGAGGGGAT CCGCGCGAGG CAGACCCCAA CCCCAACCCC
1901 AACCCCCTCC CAAACCCCAC CCAAACCCAA CCAACCCCCA ACCAAACTTT
1951 TTCTCCCAAC CCCAACCCCA ACCCCAACCC CAACCCCAAC CCCCCTCGAG
2001 GTCGACGGTA TCGATAAGCT TGATCTGTGG AATGTGTGTC AGTTAGGGTG
2051 TGGAAAGTCC CCAGGCTCCC CAGCAGGCAG AAGTATGCAA AGCATGCATC
2101 TCAATTAGTC AGCAACCAGG TGTGGAAAGT CCCCAGGCTC CCCAGCAGGC
2151 AGAAGTATGC AAAGCATGCA TCTCAATTAG TCAGCAACCA TAGTCCCGCC
2201 CCTAACTCCG CCCATCCCGC CCTAACTCC GCCCAGTTCC GCCCATTCTC
2251 CGCCCCATGG CTGACTAATT TTTTTTATTT ATGCAGAGGC CGAGGCCGCG
2301 GCCTCTGAGC TATTCCAGAA GTAGTGAGGA GGCTTTTTTG GAGGCCTAGG
2351 CTTTTGCAAA AAGCTTGCAT GCCTGCAGGT CGGCCGCCAC GACCGGTGCC
2401 GCCACCATCC CCTGACCCAC GCCCCTGACC CCTCACAAGG AGACGACCTT
2451 CCATGACCGA GTACAAGCCC ACGGTGCGCC TCGCCACCCG CGACGACGTC
2501 CCCCGGGCCG TACGCACCCT CGCCGCCGCG TTCGCCGACT ACCCCGCCAC
2551 GCGCCACACC GTCGACCCGG ACCGCCACAT CGAGCGGGTC ACCGAGCTGC
2601 AAGAACTCTT CCTCACGCGC GTCGGGCTCG ACATCGGCAA GGTGTGGGTC
2651 GCGGACGACG GCGCCGCGGT GGCGGTCTGG ACCACGCCGG AGAGCGTCGA
2701 AGCGGGGGCG GTGTTCGCCG AGATCGGCCC GCGCATGGCC GAGTTGAGCG
2751 GTTCCCGGCT GGCCGCGCAG CAACAGATGG AAGGCCTCCT GGCGCCGCAC
```

Figure 2

```
2801 CGGCCCAAGG AGCCCGCGTG GTTCCTGGCC ACCGTCGGCG TCTCGCCCGA
2851 CCACCAGGGC AAGGGTCTGG GCAGCGCCGT CGTGCTCCCC GGAGTGGAGG
2901 CGGCCGAGCG CGCCGGGGTG CCCGCCTTCC TGGAGACCTC CGCGCCCCGC
2951 AACCTCCCCT TCTACGAGCG GCTCGGCTTC ACCGTCACCG CCGACGTCGA
3001 GGTGCCCGAA GGACCGCGCA CCTGGTGCAT GACCCGCAAG CCCGGTGCCT
3051 GACGCCCGCC CCACGACCCG CAGCGCCCGA CCGAAGGAG CGCACGACCC
3101 CATGGCTCCG ACCGAAGCCA CCCGGGGCGG CCCCGCCGAC CCCGCACCCG
3151 CCCCCGAGGC CCACCGACTC TAGAGGATCA TAATCAGCCA TACCACATTT
3201 GTAGAGGTTT TACTTGCTTT AAAAAACCTC CACACCTCC CCCTGAACCT
3251 GAAACATAAA ATGAATGCAA TTGTTGTTGT TAACTTGTTT ATTGCAGCTT
3301 ATAATGGTTA CAAATAAAGC AATAGCATCA CAAATTTCAC AAATAAAGCA
3351 TTTTTTTCAC TGCATTCTAG TTGTGGTTTG TCCAAACTCA TCAATGTATC
3401 TTATCATGTC TGCCTGGCTT GAGGCTCAGG ACGCAAATCT TGAGGATGTT
3451 CAGCGGGAGT TTTCCGGGCT GCGAGTAATT GGTGATGAGG ACGAGGATGG
3501 TTCGGAGGAT GGGGAATTTT CAGACCTGGA TCTGTCTGAC AGCGACCATG
3551 AAGGGGATGA GGGTGGGGGG GCTGTTGGAG GGGCAGGAG TCTGCACTCC
3601 CTGTATTCAC TGAGCGTCGT CTAATAAAGA TGTCTATTGA TCTCTTTTAG
3651 TGTGAATCAT GTCTGACGAG GGGCCAGGTA CAGGACCTGG AAATGGCCTA
3701 GGAGAGAAGG GAGACACATC TGGACCAGAA GGCTCCGGCG CAGTGGACC
3751 TCAAAGAAGA GGGGGTGATA ACCATGGACG AGGACGGGGA AGAGGACGAG
3801 GACGAGGAGG CGGAAGACCA GGAGCCCCGG GCGGCTCAGG ATCAGGGCCA
3851 AGACATAGAG ATGGTGTCCG GAGACCCCAA AAACGTCCAA GTTGCATTGG
3901 CTGCAAAGGG ACCCACGGTG GAACAGGAGC AGGAGCAGGA GCGGGAGGGG
3951 CAGGAGGGGC AGGAGCAGGA GGGGCAGGAG GGGCAGGAGC AGGAGGGGCA
4001 GGAGGGGCAG GAGCAGGAGG AGGGGCAGGA GGGGCAGGAG CAGGAGGAGG
4051 GGCAGGAGGG GCAGGAGCAG GAGGGGCAGG AGGGGCAGGA GCAGGAGGGG
4101 CAGGAGGGGC AGGAGCAGGA GGGGCAGGAG GGGCAGGAGC AGGAGGAGGG
4151 GCAGGAGCAG GAGGGGCAGG AGCAGGAGGT GGAGGCCGGG GTCGAGGAGG
4201 CAGTGGAGGC CGGGGTCGAG GAGGTAGTGG AGGCCGGGGT CGAGGAGGTA
4251 GTGGAGGCCG CCGGGGTAGA GGACGTGAAA GAGCCAGGGG GGGAAGTCGT
4301 GAAAGAGCCA GGGGGAGAGG TCGTGGACGT GGAGAAAAGA GGCCCAGGAG
4351 TCCCAGTAGT CAGTCATCAT CATCCGGGTC TCCACCGCGC AGGCCCCTC
4401 CAGGTAGAAG GCCATTTTTC CACCCTGTAG GGAAGCCGA TTATTTTGAA
4451 TACCACCAAG AAGGTGGCCC AGATGGTGAG CCTGACGTGC CCCGGGAGC
4501 GATAGAGCAG GGCCCCGCAG ATGACCCAGG AGAAGGCCCA AGCACTGGAC
4551 CCCGGGGTCA GGGTGATGGA GGCAGGCGCA AAAAAGGAGG GTGGTTTGGA
4601 AAGCATCGTG GTCAAGGAGG TTCCAACCCG AAATTTGAGA ACATTGCAGA
4651 AGGTTTAAGA GCTCTCCTGG CTAGGAGTCA CGTAGAAAGG ACTACCGACG
4701 AAGGAACTTG GGTCGCCGGT GTGTTCGTAT ATGGAGGTAG TAAGACCTCC
4751 CTTTACAACC TAAGGCGAGG AACTGCCCTT GCTATTCCAC AATGTCGTCT
4801 TACACCATTG AGTCGTCTCC CCTTTGGAAT GGCCCTGGA CCCGGCCCAC
4851 AACCTGGCCC GCTAAGGGAG TCCATTGTCT GTTATTTCAT GGTCTTTTTA
4901 CAAACTCATA TATTTGCTGA GGTTTTGAAG GATGCGATTA AGGACCTTGT
4951 TATGACAAAG CCCGCTCCTA CCTGCAATAT CAGGGTGACT GTGTGCAGCT
5001 TTGACGATGG AGTAGATTTG CCTCCCTGGT TTCCACCTAT GGTGGAAGGG
5051 GCTGCCGCGG AGGGTGATGA CGGAGATGAC GGAGATGAAG GAGGTGATGG
5101 AGATGAGGGT GAGGAAGGGC AGGAGTGATG TAACTTGTTA GGAGACGCCC
5151 TCAATCGTAT TAAAAGCCGT GTATTCCCCC GCACTAAAGA ATAAATCCCC
5201 AGTAGACATC ATGCGTGCTG TTGGTGTATT TCTGGCCATC TGTCTTGTCA
5251 CCATTTTCGT CCTCCCAACA TGGGGCAATT GGGCATACCC ATGTTGTCAC
5301 GTCACTCAGC TCCGCGCTCA ACACCTTCTC GCGTTGGAAA ACATTAGCGA
5351 CATTTACCTG GTGAGCAATC AGACATGCGA CGGCTTTAGC CTGGCCTCCT
5401 TAAATTCACC TAAGAATGGG AGCAACCAGC AGGAAAAGGA CAAGCAGCGA
5451 AAATTCACGC CCCCTTGGGA GGTGGCGGCA TATGCAAAGG ATAGCACTCC
5501 CACTCTACTA CTGGGTATCA TATGCTGACT GTATATGCAT GAGGATAGCA
5551 TATGCTACCC GGATACAGAT TAGGATAGCA TATACTACCC AGATATAGAT
```

Figure 2 (cont.)

```
5601 TAGGATAGCA TATGCTACCC AGATATAGAT TAGGATAGCC TATGCTACCC
5651 AGATATAAAT TAGGATAGCA TATACTACCC AGATATAGAT TAGGATAGCA
5701 TATGCTACCC AGATATAGAT TAGGATAGCC TATGCTACCC AGATATAGAT
5751 TAGGATAGCA TATGCTACCC AGATATAGAT TAGGATAGCA TATGCTATCC
5801 AGATATTTGG GTAGTATATG CTACCCAGAT ATAAATTAGG ATAGCATATA
5851 CTACCCTAAT CTCTATTAGG ATAGCATATG CTACCCGGAT ACAGATTAGG
5901 ATAGCATATA CTACCCAGAT ATAGATTAGG ATAGCATATG CTACCCAGAT
5951 ATAGATTAGG ATAGCCTATG CTACCCAGAT ATAAATTAGG ATAGCATATA
6001 CTACCCAGAT ATAGATTAGG ATAGCATATG CTACCCAGAT ATAGATTAGG
6051 ATAGCCTATG CTACCCAGAT ATAGATTAGG ATAGCATATG CTATCCAGAT
6101 ATTTGGGTAG TATATGCTAC CCATGGCAAC ATTAGCCCAC CGTGCTCTCA
6151 GCGACCTCGT GAATATGAGG ACCAACAACC CTGTGCTTGG CGCTCAGGCG
6201 CAAGTGTGTG TAATTTGTCC TCCAGATCGC AGCAATCGCG CCCCTATCTT
6251 GGCCCGCCCA CCTACTTATG CAGGTATTCC CCGGGGTGCC ATTAGTGGTT
6301 TTGTGGGCAA GTGGTTTGAC CGCAGTGGTT AGCGGGGTTA CAATCAGCCA
6351 AGTTATTACA CCCTTATTTT ACAGTCCAAA ACCGCAGGGC GGCGTGTGGG
6401 GGCTGACGCG TGCCCCCACT CCACAATTTC AAAAAAAAGA GTGGCCACTT
6451 GTCTTTGTTT ATGGGCCCCA TTGGCGTGGA GCCCCGTTTA ATTTTCGGGG
6501 GTGTTAGAGA CAACCAGTGG AGTCCGCTGC TGTCGGCGTC CACTCTCTTT
6551 CCCCTTGTTA CAAATAGAGT GTAACAACAT GGTTCACCTG TCTTGGTCCC
6601 TGCCTGGGAC ACATCTTAAT AACCCCAGTA TCATATTGCA CTAGGATTAT
6651 GTGTTGCCCA TAGCCATAAA TTCGTGTGAG ATGGACATCC AGTCTTTACG
6701 GCTTGTCCCC ACCCCATGGA TTTCTATTGT TAAAGATATT CAGAATGTTT
6751 CATTCCTACA CTAGTATTTA TTGCCCAAGG GGTTTGTGAG GGTTATATTG
6801 GTGTCATAGC ACAATGCCAC CACTGAACCC CCCGTCCAAA TTTTATTCTG
6851 GGGGCGTCAC CTGAAACCTT GTTTTCGAGC ACCTCACATA CACCTTACTG
6901 TTCACAACTC AGCAGTTATT CTATTAGCTA AACGAAGGAG AATGAAGAAG
6951 CAGGCGAAGA TTCAGGAGAG TTCACTGCCC GCTCCTTGAT CTTCAGCCAC
7001 TGCCCTTGTG ACTAAAATGG TTCACTACCC TCGTGGAATC CTGACCCCAT
7051 GTAAATAAAA CCGTGACAGC TCATGGGGTG GGAGATATCG CTGTTCCTTA
7101 GGACCCTTTT ACTAACCCTA ATTCGATAGC ATATGCTTCC CGTTGGGTAA
7151 CATATGCTAT TGAATTAGGG TTAGTCTGGA TAGTATATAC TACTACCCGG
7201 GAAGCATATG CTACCCGTTT AGGGTTAACA AGGGGGCCTT ATAAACACTA
7251 TTGCTAATGC CCTCTTGAGG GTCCGCTTAT CGGTAGCTAC ACAGGCCCCT
7301 CTGATTGACG TTGGTGTAGC CTCCCGTAGT CTTCCTGGGC CCCTGGGAGG
7351 TACATGTCCC CCAGCATTGG TGTAAGAGCT TCAGCCAAGA GTTACACATA
7401 AAGGCAATGT TGTGTTGCAG TCCACAGACT GCAAAGTCTG CTCCAGGATG
7451 AAAGCCACTC AGTGTTGGCA AATGTGCACA TCCATTTATA AGGATGTCAA
7501 CTACAGTCAG AGAACCCCTT TGTGTTTGGT CCCCCCCCGT GTCACATGTG
7551 GAACAGGGCC CAGTTGGCAA GTTGTACCAA CCAACTGAAG GGATTACATG
7601 CACTGCCCCG CGAAGAAGGG GCAGAGATGT CGTAGTCAGG TTTAGTTCGT
7651 CCGGGGCGGG GATCGATCCT CTAGAGTCGA CCTCATGGCT GCGCCCCGAC
7701 ACCCGCCAAC ACCCGCTGAC GCGCCCTGAC GGGCTTGTCT GCTCCCGGCA
7751 TCCGCTTACA GACAAGCTGT GACCGTCTCC GGGAGCTGCA TGTGTCAGAG
7801 GTTTTCACCG TCATCACCGA AACGCGCGAG GCAGCCGGAT CATAATCAGC
7851 CATACCACAT TTGTAGAGGT TTTACTTGCT TTAAAAAACC TCCCACACCT
7901 CCCCCTGAAC CTGAAACATA AAATGAATGC AATTGTTGTT GTTAACTTGT
7951 TTATTGCAGC TTATAATGGT TACAAATAAA GCAATAGCAT CACAAATTTC
8001 ACAAATAAAG CATTTTTTTC ACTGCATTCT AGTTGTGGTT TGTCCAAACT
8051 CATCAATGTA TCTTATCATG TCTGGATCGA TCCACTAGTT CTAGAGCGGC
8101 CGCCACCGCG GTGGAGCTCC AGCTTTTGTT CCCTTTAGTG AGGGTTAATT
8151 TCGAGCTTGG CGTAATCATG GTCATAGCTG TTTCCTGTGT GAAATTGTTA
8201 TCCGCTCACA ATTCCACACA ACATACGAGC CGGAAGCATA AAGTGTAAAG
8251 CCTGGGGTGC CTAATGAGTG AGCTAACTCA CATTAATTGC GTTGCGCTCA
8301 CTGCCCGCTT TCCAGTCGGG AAACCTGTCG TGCCAGCTGC ATTAATGAAT
8351 CGGCCAACGC GCGGGGAGAG GCGGTTTGCG TATTGGGCGC TCTTCCGCTT
```

Figure 2 (cont.)

```
8401 CCTCGCTCAC TGACTCGCTG CGCTCGGTCG TTCGGCTGCG GCGAGCGGTA
8451 TCAGCTCACT CAAAGGCGGT AATACGGTTA TCCACAGAAT CAGGGGATAA
8501 CGCAGGAAAG AACATGTGAG CAAAAGGCCA GCAAAAGGCC AGGAACCGTA
8551 AAAAGGCCGC GTTGCTGGCG TTTTTCCATA GGCTCCGCCC CCCTGACGAG
8601 CATCACAAAA ATCGACGCTC AAGTCAGAGG TGGCGAAACC CGACAGGACT
8651 ATAAAGATAC CAGGCGTTTC CCCCTGGAAG CTCCCTCGTG CGCTCTCCTG
8701 TTCCGACCCT GCCGCTTACC GGATACCTGT CCGCCTTTCT CCCTTCGGGA
8751 AGCGTGGCGC TTTCTCATAG CTCACGCTGT AGGTATCTCA GTTCGGTGTA
8801 GGTCGTTCGC TCCAAGCTGG GCTGTGTGCA CGAACCCCCC GTTCAGCCCG
8851 ACCGCTGCGC CTTATCCGGT AACTATCGTC TTGAGTCCAA CCCGGTAAGA
8901 CACGACTTAT CGCCACTGGC AGCAGCCACT GGTAACAGGA TTAGCAGAGC
8951 GAGGTATGTA GGCGGTGCTA CAGAGTTCTT GAAGTGGTGG CCTAACTACG
9001 GCTACACTAG AAGAACAGTA TTTGGTATCT GCGCTCTGCT GAAGCCAGTT
9051 ACCTTCGGAA AAAGAGTTGG TAGCTCTTGA TCCGGCAAAC AAACCACCGC
9101 TGGTAGCGGT GGTTTTTTTG TTTGCAAGCA GCAGATTACG CGCAGAAAAA
9151 AAGGATCTCA AGAAGATCCT TTGATCTTTT CTACGGGGTC TGACGCTCAG
9201 TGGAACGAAA ACTCACGTTA AGGGATTTTG GTCATGAGAT TATCAAAAAG
9251 GATCTTCACC TAGATCCTTT TAAATTAAAA ATGAAGTTTT AAATCAATCT
9301 AAAGTATATA TGAGTAAACT TGGTCTGACA GTTACCAATG CTTAATCAGT
9351 GAGGCACCTA TCTCAGCGAT CTGTCTATTT CGTTCATCCA TAGTTGCCTG
9401 ACTCCCCGTC GTGTAGATAA CTACGATACG GGAGGGCTTA CCATCTGGCC
9451 CCAGTGCTGC AATGATACCG CGAGACCCAC GCTCACCGGC TCCAGATTTA
9501 TCAGCAATAA ACCAGCCAGC CGGAAGGGCC GAGCGCAGAA GTGGTCCTGC
9551 AACTTTATCC GCCTCCATCC AGTCTATTAA TTGTTGCCGG GAAGCTAGAG
9601 TAAGTAGTTC GCCAGTTAAT AGTTTGCGCA ACGTTGTTGC CATTGCTACA
9651 GGCATCGTGG TGTCACGCTC GTCGTTTGGT ATGGCTTCAT TCAGCTCCGG
9701 TTCCCAACGA TCAAGGCGAG TTACATGATC CCCCATGTTG TGCAAAAAAG
9751 CGGTTAGCTC CTTCGGTCCT CCGATCGTTG TCAGAAGTAA GTTGGCCGCA
9801 GTGTTATCAC TCATGGTTAT GGCAGCACTG CATAATTCTC TTACTGTCAT
9851 GCCATCCGTA AGATGCTTTT CTGTGACTGG TGAGTACTCA ACCAAGTCAT
9901 TCTGAGAATA GTGTATGCGG CGACCGAGTT GCTCTTGCCC GGCGTCAATA
9951 CGGGATAATA CCGCGCCACA TAGCAGAACT TTAAAAGTGC TCATCATTGG
10001AAAACGTTCT TCGGGGCGAA AACTCTCAAG GATCTTACCG CTGTTGAGAT
10051CCAGTTCGAT GTAACCCACT CGTGCACCCA ACTGATCTTC AGCATCTTTT
10101ACTTTCACCA GCGTTTCTGG GTGAGCAAAA ACAGGAAGGC AAAATGCCGC
10151AAAAAAGGGA ATAAGGGCGA CACGGAAATG TTGAATACTC ATACTCTTCC
10201TTTTTCAATA TTATTGAAGC ATTTATCAGG GTTATTGTCT CATGAGCGGA
10251TACATATTTG AATGTATTTA GAAAAATAAA CAAATAGGGG TTCCGCGCAC
10301ATTTCCCCGA AAAGTGCCAC CTAAATTGTA AGCGTTAATA TTTTGTTAAA
10351ATTCGCGTTA AATTTTTGTT AAATCAGCTC ATTTTTTAAC CAATAGGCCG
10401AAATCGGCAA AATCCCTTAT AAATCAAAAG AATAGACCGA GATAGGGTTG
10451 AGTG
```

Figure 2 (cont.)

Circular EBVp          Circular Eplus
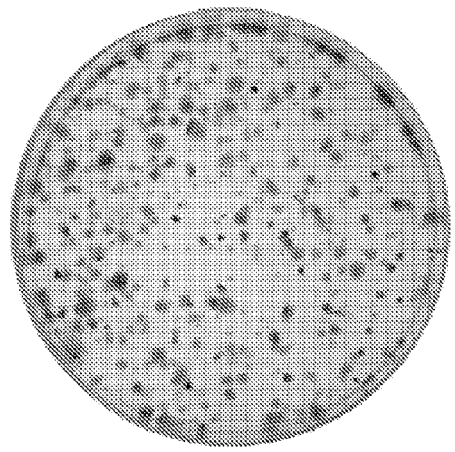 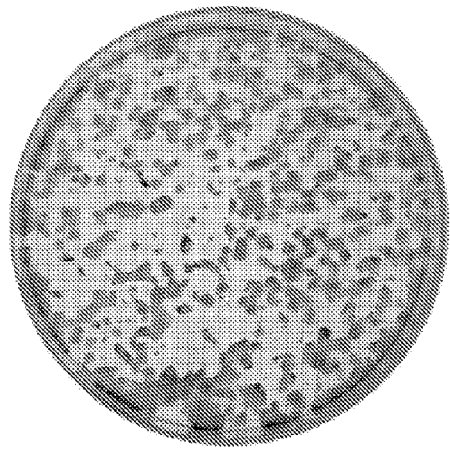
Figure 3

EPISOMAL EXPRESSION VECTOR FOR METAZOAN CELLS

CROSS REFERENCE TO RELATED APPLICATIONS

This application is a National Stage filing under 35 U.S.C. §371(c) of International Application Serial No. PCT/US07/71911 filed Jun. 22, 2007, which, in turn, claims priority benefit under 35 U.S.C. §119(e) of U.S. Provisional Patent Application Ser. No. 60/815,724 filed Jun. 22, 2006. The disclosures of both applications are incorporated herein by reference.

FIELD OF THE INVENTION

The present invention relates to an episomal expression vector comprising an origin of replication for episomal maintenance in a metazoan cell, a gene for episomal maintenance, and a telomeric polynucleotide sequence. The vector is useful for stable transfection of human and animal cells. The vector can be used for many applications such as cloned gene expression/regulation, consisting of large genomic clones; recombinant protein overexpression; cDNA clones; stem cell engineering/transgenics, stem cell lines and/or whole organism; non-viral delivery gene therapy; and DNA vaccines/immunogen production.

BACKGROUND

Many plasmid vectors are currently available for expression in animal cells. Commercial providers of such vectors include Invitrogen (Carlsbad, Calif.), Promega (Madison, Wis.) and Clontech (Mountain View, Calif.). In general, the two key elements in these vectors are a strong promoter and a convenient multiple cloning site (MCS) for insertion of genes of interest. Using such vectors, transient expression of the target gene can be readily achieved in short term cultures.

However, in order to achieve sustained high levels of gene expression, vectors are preferred that contain a selectable marker to grow and maintain stable transfectants. In order to achieve replication and propagation in daughter cells, the recombinant plasmid must integrate into the host genome after transfection. This event is relatively rare and rate limiting as well as subject to the vagaries of each particular site of integration (Al Shawi R., Kinnaird J., Burke J. and Bishop J. O. 1990. Expression of a foreign gene in a line of transgenic mice is modulated by a chromosomal position effect. Mol. Cell. Biol. 10:1192-1198).

To circumvent the consequences of genomic integration altogether, vectors capable of autonomous replication and adequate segregation during cell division can be employed. This vector category includes Mammalian Artificial Chromosomes (MACs) (Lindenbaum M, Perkins E, Csonka E, Fleming E, Garcia L, Greene A, Gung L, Hadlaczky G, Lee E, Leung J, MacDonald N, Maxwell A, Mills K, Monteith D, Perez C F, Shellard J, Stewart S, Stodola T, Vandenborre D, Vanderbyl S, Ledebur HC Jr. 2004. A mammalian artificial chromosome engineering system (ACE System) applicable to biopharmaceutical protein production, transgenesis and gene-based cell therapy. Nucleic Acids Res. 32(21):e172) and episomal vectors such as plasmids derived from the Epstein-Barr virus (EBV). EBV-derived plasmids can be stably maintained in dividing cells through the use of the viral replication and segregation elements (Yates, J. L., Warren, N., and Sugden, B. 1985. Stable replication of plasmids derived from Epstein-Barr virus in various mammalian cells. Nature 313: 812-815).

An advantage of episomal vectors over MACs is that they are maintained at multiple copies per cell (Conese, M., Auriche, C., and Ascenzioni, F. 2004. Gene therapy progress and prospects: episomally maintained self-replicating systems. Gene Ther. 24:1735-1741), thus naturally enhancing expression levels. The relatively smaller EBV-derived plasmids (10-100 kb in size) can also be shuttled from the mammalian host cell back into bacteria for analysis or propagation (Kelleher Z. T., Fu H., Livanos E., Wendelburg B., Gulino S. and Vos J. M. 1998. Epstein-Barr-based episomal chromosomes shuttle 100 kb of self-replicating circular human DNA in mouse cells. Nat. Biotechnol. 16:762-768; Wade-Martins R., Frampton J. and James M. R. 1999. Long-term stability of large insert genomic DNA episomal shuttle vectors in human cells. Nucleic Acids Res. 27:1674-1682). In contrast, the relatively larger MACs (>1 Mb in size) have to be propagated in suitable mammalian host cells. Finally, plasmids can be more readily defined in that their entire sequence can be determined at each step of development using standard techniques and molecular biology tools. In contrast, only a small percentage of a MAC can be known with certainty at any point by direct sequencing, and structural analysis of MACs requires sophisticated techniques such as flourescence in situ hybridization (FISH) and flow cytometry.

There is currently a need for more flexible but powerful expression vectors to address an expanding market for complex glycosylated proteins. There is also a need for efficient non-viral gene delivery systems for many transgenic applications and in gene therapy. The disclosed invention, a novel episomal vector design, has the desired characteristics to meet these needs.

SUMMARY OF THE INVENTION

The invention relates to a vector comprising an origin of replication for episomal maintenance in a metazoan cell, a gene for episomal maintenance in the metazoan cell, and a telomeric polynucleotide sequence.

In one embodiment, the vector comprises a polynucleotide sequence encoding a selectable marker for expression and growth advantage in a metazoan cell.

In one embodiment, the vector comprises an origin of replication for episomal maintenance in a prokaryotic cell.

In one embodiment, wherein the vector comprises a polynucleotide sequence encoding a selectable marker for expression and growth advantage in a prokaryotic cell, the polynucleotide sequence operably linked to a promoter.

In one embodiment, the vector comprises a polynucleotide sequence comprising a multiple cloning site (MCS).

In one embodiment, the vector comprises a heterologous polynucleotide sequence.

In one embodiment, the telomeric polynucleotide sequence is from an organism selected from the group consisting of mammals such as human or mouse, *Tetrahymena*, *Euplotes*, *Oxytricha*, *Saccharomyces cerevisiae*, and *Kluyveromyces lactis*.

In one embodiment, the origin of replication for episomal maintenance in the metazoan cell is and the gene for episomal maintenance in the metazoan cell are respectively selected from the group consisting of OriP and EBNA-1 latency genes from Epstein-Barr Virus (EBV); origin of the Kaposi's sarcoma associated herpesvirus (KSHV) and the gene for nuclear antigen 1 of KSHV (LANA-1); and origin of the Bovine papillomavirus (BPV) and the gene for E2 from BPV.

In one embodiment, the vector comprises a polynucleotide sequence encoding a selectable marker for expression and growth advantage in a metazoan cell wherein the selectable marker for expression and growth advantage in a metazoan cell is selected from the group consisting of puromycin-N-acetyl-transferase (PAC) gene, hygromycin phosphotransferase B gene, aminoglycoside phosphotransferase II gene, and Zeocin resistance gene.

In one embodiment, the vector comprises a polynucleotide sequence encoding a selectable marker for expression and growth advantage in a metazoan cell wherein the selectable marker for expression and growth advantage in a metazoan cell wherein the selectable marker is operably linked to an early promoter of SV40 and a SV40 polyadenylation signal.

In one embodiment, the vector comprises an origin of replication for episomal maintenance in a prokaryotic cell wherein the origin of replication for episomal maintenance in a prokaryotic cell is a bacterial ColE1 origin of replication.

In one embodiment, the vector comprises a polynucleotide sequence encoding a selectable marker for expression and growth advantage in a prokaryotic cell, wherein the selectable marker for expression and growth advantage in a prokaryotic cell is an antibiotic resistance gene. Representative examples include the group consisting of ampicillin resistance gene, tetracycline resistance gene, kanamycin resistance gene, chloramphenicol resistance gene, erythromycin resistance gene, zeocine resistance gene, neomycin resistance gene, hygromycin resistance gene and methotrexate resistance gene.

In one embodiment, the telomeric polynucleotide sequence is a region of repetitive sequence that is relatively rich in guanine.

In one embodiment, the telomeric polynucleotide sequence is selected from the group consisting of 5'-TTGGGG-3' (SEQ ID NO: 1); 5'-TTTTGGGG-3' (SEQ ID NO: 2); 5'-TTAGGG-3' (SEQ ID NO: 3); 5'-TGGG-3' (SEQ ID NO: 6); and 5'-TGGTGTACGGA-3' (SEQ ID NO: 14).

In one embodiment, the vector comprises a polynucleotide sequence comprising a multiple cloning site (MCS), the vector comprising two inverted repeat regions comprising the telomeric polynucleotide sequence flanking the MCS.

In one embodiment, the inverted repeat regions comprise 2 to about 100 consecutive copies of the telomeric polynucleotide.

In one embodiment, the inverted repeat regions comprises about 33 consecutive copies of the telomeric polynucleotide.

In one embodiment, the inverted repeat regions comprises about 50 consecutive copies of the telomeric polynucleotide.

In one embodiment, the vector comprises a heterologous polynucleotide sequence.

In one embodiment, the vector comprises a polynucleotide sequence selected from the group consisting of SEQ ID NO: 16.

The invention also relates to a host cell transformed with the vector according to present invention.

The invention also relates to a method of producing an RNA molecule comprising contacting a host cell with the vector according to the present invention; and culturing the host cell under suitable culture conditions such that the RNA molecule is transcribed.

The invention also relates to a method of producing a polypeptide comprising contacting a host cell with the vector according to the present invention, wherein the heterologous polynucleotide sequence encodes the polypeptide; and culturing the host cell under suitable culture conditions such that the polypeptide is expressed.

BRIEF DESCRIPTION OF THE DRAWINGS

FIG. 2. Complete sequence of the Eplus vector prototype, pEP2. (SEQ. ID NO: 16)

FIG. 3. Puromycin resistant colonies of SV.RNS/HF-1 cells transfected with either Ep2 or an episomal control vector.

DETAILED DESCRIPTION OF THE INVENTION

Figure 1:
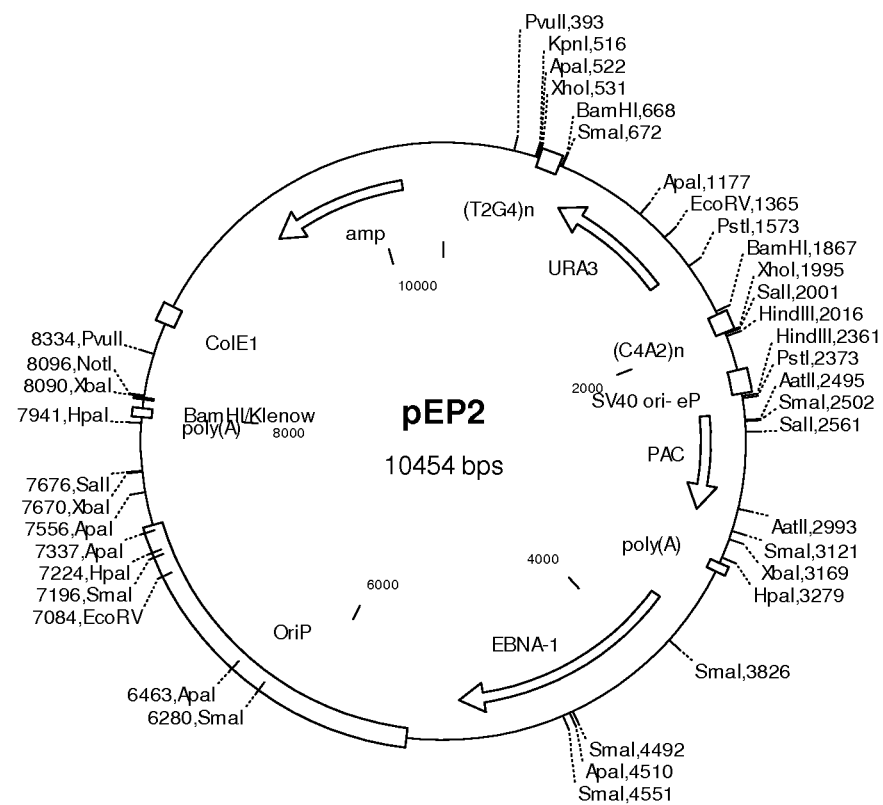
FIG. 1. Map of the prototype Eplus vector, pEP2.

The invention as disclosed and described herein, provides a vector comprising an origin of replication for episomal maintenance in a metazoan cell, a gene for episomal maintenance in the metazoan cell, and a telomeric polynucleotide sequence.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

The term "protein coding sequence" means a nucleotide sequence encoding a polypeptide gene which can be used to distinguish cells expressing the polypeptide gene from those not expressing the polypeptide gene.

An "episome" is a genetic element that can replicate free in the cytoplasm of a cell. "Episomal maintenance" occurs when the episome can be replicated and transcribed and the episome is not inserted into a chromosome. The episome is usually a circular polynucleotide. The term "replication" means duplication of a vector.

A metazoan cell is a cell from a multicellular animal of the subkingdom Metazoa, a division of the animal kingdom in traditional two-kingdom classification systems.

In one embodiment, the origin of replication for episomal maintenance in the metazoan cell is and the gene for episomal maintenance in the metazoan cell are respectively selected from the group consisting of OriP and EBNA-1 latency genes from Epstein-Barr Virus (EBV); origin of the Kaposi's sarcoma associated herpesvirus (KSHV) and the gene for nuclear antigen 1 of KSHV (LANA-1); and origin of the Bovine papillomavirus (BPV) and the gene for E2 from BPV.

"Telomeric sequences" or "telomeres" are repetitive DNA sequences found at the ends of linear chromosomes in eukaryotes (Fajkus J., Sykorova E., Leitch A. R. 2005 Telomeres in evolution and evolution of telomeres. Chromosome Res. 13:469-79). Telomeres are essential to stabilize the exposed chromosomal ends and ensure proper segregation during mitosis. Telomeres are also subject to attrition (shortening) during chromosome replication, a process that is reversed by elongation of the telomeric repeats through the action of telomerase, a RNA-directed DNA polymerase (O'Reilly M., Teichmann S. A., Rhodes D. 1999 Telomerases. Curr. Opin. Struct. Biol. 9:56-65). Tables 1A and 1B show a list of known telomeric repeat units and their relation to the RNA template sequence in the corresponding telomerase.

TABLE 1A

Telomeric repeat sequence units in various eukaryotes and the RNA template sequence used by telomerase to synthesize them.

| Organism | Telomere sequence repeat unit | Telomerase RNA template sequence |
| --- | --- | --- |
| Tetrahymena | TTGGGG (SEQ ID NO: 1) | CAACCCCAA (SEQ ID NO: 8) |
| Euplotes | TTTTGGGG (SEQ ID NO: 2) | CAAAACCCCAAAACC (SEQ ID NO: 9) |
| Oxytricha | TTTTGGGG (SEQ ID NO: 2) | CAAAACCCCAAAACC (SEQ ID NO: 9) |
| Human | TTAGGG (SEQ ID NO: 3) | CUAACCCUAAC (SEQ ID NO: 10) |
| Mouse | TTAGGG (SEQ ID NO: 3) | CCUAACCCU (SEQ ID NO: 11) |
| Saccharomyces cerevisiae | TG (SEQ ID NO: 4); TGG (SEQ ID NO: 5); or TGGG (SEQ ID NO: 6) | CACCACACCCACACAC (SEQ ID NO: 12) |
| Kluyveromyces lactis | TTTGATTAGGTATG TGGTGTACGGA (SEQ ID NO: 7) | UCAAAUCCGUACACCAC AUACCUAAUCAAA (SEQ ID NO: 13) |

TABLE 1B

Telomeric repeat sequence units in various eukaryotes.

| Slime moulds | Dictyostelium | AG (1-8) (SEQ ID NO: 17) |
| --- | --- | --- |
| Ciliate protozoa | Paramecium | TTGGG(T/G) (SEQ ID NO: 18) |
| Apicomplexan protozoa | Plasmodium | TTAGGG(T/C) (SEQ ID NO: 19) |
| Higher plants | Arabidopsis thaliana | TTTAGGG (SEQ ID NO: 20) |
| Green algae | Chlamydomonas | TTTTAGGG (SEQ ID NO: 21) |
| Insects | Bombyx mori | TTAGG (SEQ ID NO: 22) |
| Roundworms | Ascaris lumbricoides | TTAGGC (SEQ ID NO: 23) |

TABLE 1B-continued

Telomeric repeat sequence units in various eukaryotes.

| | | |
|---|---|---|
| Fission yeasts | *Schizosaccharomyces pombe* | TTAC(A)(C)G(1-8) (SEQ ID NO: 24) |
| Budding yeasts | *Saccharomyces cerevisiae* | TGTGGGTGTGGTG (SEQ ID NO: 25; from RNA template) or G(2-3)(TG)(1-6)T (SEQ ID NO: 26; consensus) |
| | *Candida glabrata* | GGGGTCTGGGTGCTG (SEQ ID NO: 27) |
| | *Candida albicans* | GGTGTACGGATGTCTAACTTCTT (SEQ ID NO: 28) |
| | *Candida tropicalis* | GGTGTA[C/A]GGATGTCACGATCATT (SEQ ID NO: 29) |
| | *Candida maltosa* | GGTGTACGGATGCAGACTCGCTT (SEQ ID NO: 30) |
| | *Candida guillermondii* | GGTGTAC (SEQ ID NO: 31) |
| | *Candida pseudotropicalis* | GGTGTACGGATTTGATTAGTTATGT (SEQ ID NO: 33) |
| | *Kluyveromyces lactis* | GGTGTACGGATTTGATTAGGTATGT (SEQ ID NO: 32) |

In one embodiment, the telomeric polynucleotide sequence is a region of repetitive sequence that is relatively rich in guanine. Relatively rich means a sequence of at least 6 nucleotides that is constitutes greater than 25%, 30%, 35%, 40%, 45%, 50%, 55%, or 60% guanine.

In one embodiment, the telomeric polynucleotide sequence is from an organism selected from the group consisting of mammals such as human or mouse, *Tetrahymena, Euplotes, Oxytricha, Saccharomyces cerevisiae*, and *Kluyveromyces lactis*.

In one embodiment, the telomeric polynucleotide sequence is selected from the group consisting of 5'-TTGGGG-3' (SEQ ID NO: 1); 5'-TTTTGGGG-3' (SEQ ID NO: 2); 5'-TTAGGG-3' (SEQ ID NO: 3); 5'-TGGG-3' (SEQ ID NO: 6); 5'-TGGTGTACGGA-3' (SEQ ID NO: 14); and SEQ ID NOS: 17-32.

In one embodiment, the vector comprises a polynucleotide sequence comprising a multiple cloning site (MCS) to facilitate the insertion of DNA sequence(s) containing a heterologous gene into the cloning vector. In general, the multiple cloning site includes "rare" restriction enzyme sites; i.e., sites which are found in eukaryotic genes at a frequency of from about one in every 10,000 to about one in every 100,000 base pairs. An appropriate vector is thus formed by cutting the cloning vector by standard techniques at appropriate restriction sites in the multiple cloning site, and then ligating the DNA sequence containing the heterologous gene into the cloning vector.

In one embodiment, the vector comprises two inverted repeat regions comprising the telomeric polynucleotide sequence flanking the MCS.

An "inverted repeat" or "IR" is a sequence of nucleotides that is the reversed complement of another sequence further downstream. For example, 5'-TTGGGGNNNNNNC-CCCAA-3' (SEQ ID NO: 15; N is any nucleotide).

In one embodiment, the inverted repeat regions comprise 2 to about 100 consecutive copies of the telomeric polynucleotide. In one embodiment, the inverted repeat region comprises about 33 consecutive copies of the telomeric polynucleotide. In one embodiment, the inverted repeat region comprises about 50 consecutive copies of the telomeric polynucleotide.

In one embodiment, the vector comprises a heterologous polynucleotide sequence. The term "heterologous" means a DNA sequence not found in the native vector genome.

The term "promoter" is used according to its art-recognized meaning. It is intended to mean the DNA region, usually upstream to the coding sequence of a gene or operon, which binds RNA polymerase and directs the enzyme to the correct transcriptional start site. The promoter may be constitutive or inducible. "Operably linked", when referring to DNA segments, indicates that the segments are arranged so that they function in concert e.g. the transcription process takes place via the RNA-polymerase binding to the promoter segment and proceeding with the transcription through the coding segment until the polymerase stops when it encounters a transcription terminator segment.

In one embodiment, the vector comprises a polynucleotide sequence encoding a selectable marker for expression and growth advantage in a metazoan cell. In one embodiment, wherein the vector comprises a polynucleotide sequence encoding a selectable marker for expression and growth advantage in a prokaryotic cell, the polynucleotide sequence operably linked to a promoter. A selectable marker is a gene the product of which provides for biocide, antibiotic or viral resistance, resistance to heavy metals, prototrophy to auxotrophs, and the like. Antibiotic selectable markers confer antibiotic resistance to such antibiotics as ampicillin, kanamycin, chloramphenicol, erythromycin, tetracycline, zeocine, neomycin, hygromycin or methotrexate.

In one embodiment, the vector comprises a polynucleotide sequence encoding a selectable marker for expression and growth advantage in a metazoan cell wherein the selectable marker for expression and growth advantage in a metazoan cell is selected from the group consisting of puromycin-N-acetyl-transferase (PAC) gene, hygromycin phosphotransferase B gene, aminoglycoside phosphotransferase II gene, and Zeocin resistance gene.

In one embodiment, the vector comprises a polynucleotide sequence encoding a selectable marker for expression and growth advantage in a metazoan cell wherein the selectable marker for expression and growth advantage in a metazoan cell wherein the selectable marker is operably linked to an early promoter of SV40 and a SV40 polyadenylation signal.

In one embodiment, the vector comprises an origin of replication for episomal maintenance in a prokaryotic cell. In one embodiment, the origin of replication for episomal maintenance in a prokaryotic cell is a bacterial ColE1 origin of replication.

In one embodiment, the vector comprises a polynucleotide sequence encoding a selectable marker for expression and growth advantage in a prokaryotic cell, wherein the selectable marker for expression and growth advantage in a prokaryotic cell is selected from the group consisting of ampicillin resistance gene, tetracycline resistance gene, kanamycin resistance gene, chloramphenicol resistance gene, erythromycin resistance gene, zeocine resistance gene, neomycin resistance gene, hygromycin resistance gene and methotrexate resistance gene.

In one embodiment the vector is derived from or comprises polynucleotide sequences from a virus, for example, the Epstein-Barr Virus (EBV), the Kaposi's sarcoma associated herpesvirus (KSHV), and Bovine papillomavirus (BPV).

In one embodiment the vector is derived from or comprises polynucleotide sequences from the Epstein-Barr Virus (EBV). EBV is a γ-herpesvirus frequently associated with Hodgkin's lymphomas (Nicholas J. 2000 Evolutionary aspects of oncogenic herpesviruses. Mol. Pathol. 53:222-37). EBV is capable of establishing latent infections in susceptible host cells. During latency, the viral genome is maintained as a circular DNA molecule or episome. Episome maintenance requires only two viral sequences, EBNA-1 and OriP. OriP is the replication origin that is used only once per cell cycle. EBNA-1 encodes a nuclear antigen required during mitosis for segregation of copies of the viral genome to daughter cells. Segregation is due to tethering of the viral genome to host chromosomes through nuclear antigen 1 (Sears J., Ujihara M., Wong S., Ott C., Middeldorp J., Aiyar A. 2004 The amino terminus of Epstein-Barr Virus (EBV) nuclear antigen 1 contains AT hooks that facilitate the replication and partitioning of latent EBV genomes by tethering them to cellular chromosomes. J. Virol. 78:11487-505).

EBV derived plasmids are circular DNA molecules containing the latency genes OriP and EBNA-1, thus allowing replication and mitotic segregation by "tethering" to host chromosomes in nuclear antigen-1 dependent fashion (Kanda T., Otter M., Wahl G. M. 2001. Coupling of mitotic chromosome tethering and replication competence in Epstein-Barr virus-based plasmids. Mol. Cell. Biol. 21:3576-88).

In one embodiment, the vector is an "Eplus" vector. Eplus vectors are engineered from an EBV plasmid by inclusion of telomeric repeats from Tetrahymena. These repeats produce higher rates of stable transfection in a variety of animal cells than control plasmids lacking the telomeric repeats. Eplus vectors contain the following elements: OriP and EBNA-1 genes from EBV; an SV40 early promoter (ori⁻) driving a puromycin resistance gene (PAC) as the selectable marker; ColE1 bacterial origin and ampicillin resistance gene for shuttling the vector into bacteria; two inverted repeat regions flanking a unique cloning site (BamHI), where each repeat region consist of multiple copies of the 5'-TTGGGG-3' (SEQ ID NO: 1) sequence motif or G-rich sequences such as: 5'-TTTTGGGG-3' (SEQ ID NO: 2); 5'-TTAGGG-3' (SEQ ID NO: 3); 5'-TGGG-3' (SEQ ID NO: 6); and 5'-TGGTGTACGGA-3' (SEQ ID NO: 14).

In one embodiment, the vector comprises a polynucleotide sequence selected from the group consisting of SEQ ID NO: 16. A map of the prototype Eplus vector (pEP2) is shown in FIG. 1 and its full sequence is shown in FIG. 2 (SEQ ID NO: 16). Sequences are assembled from direct sequencing of portions of pEP2 and from public databases for known regions and genes, where available. Only the top strand is shown. A description of the features contained within the sequence of the prototype vector is shown in Table 2. Start and end positions correspond to the sequence positions in FIG. 2. The disclosed sequence of pEP2 is not intended to limit the scope of the Eplus vector design in any way.

TABLE 2

Description of key features of the Eplus vector prototype, pEP2.

| Feature | Start | End | Description |
| --- | --- | --- | --- |
| (T2G4)n | 674 | 1009 | Tetrahymena telomeric repeat of unit TTGGGG |
| URA3 | 1016 | 1819 | Gene in cloning site |
| (C4A2)n | 1826 | 2185 | Tetrahymena telomeric repeat of unit CCCCAA |
| SV40 ori⁻ eP | 2405 | 2537 | SV40 origin-minus early promoter |
| PAC | 2644 | 3243 | puromycin resistance gene |
| poly(A) | 3504 | 3554 | SV40 polyadenylation signal |
| EBNA-1 | 3608 | 5533 | EBV nuclear antigen 1 gene |
| OriP | 5840 | 7775 | EBV origin of replication |
| ColE1 | 8210 | 8316 | Bacterial origin of replication |
| amp | 9890 | 9030 | Ampicillin resistance gene (complementary strand) |

A summary of known functions in the vector are as follows.

- A ColE1 origin of replication and an ampicillin-resistance gene (amp) for propagation of the vector in E. coli.
- A modified SV40 early promoter lacking large-T-antigen-dependent origin of replication activity (SV40 ori⁻ eP). This constitutive promoter directs the expression of the puromycin-N-acetyl-transferase (PAC) gene for growth of transfected cells in the presence of puromycin.
- The origin of replication (OriP) and gene encoding EBNA-1 from the Epstein-Barr virus (EBV). These elements are required for replication and episomal maintenance of the vector in transfected mammalian cells.
- Two regions of ~300 bp each containing the Tetrahymena telomeric repeat sequence T2G4 in the form of a (T2G4)n-URA3-(C4A2)n cassette. Note that digestion of the prototype vector with the restriction enzyme BamHI exposes the T2G4 repeats at the 3' ends of the linearized vector. The yeast URA3 gene is not essential for the function of the circular vector and can be replaced by any other DNA sequence flanked by BamHI restriction sites.

Additional embodiments of Eplus vectors are listed and described in Table 3. pEP1 and pEP3 are structural variants of the prototype pEP2. Vectors pEP23 to 26 are constructed by replacing the URA3 insert of pEP2 with a luciferase reporter gene.

TABLE 3

Description of disclosed plasmids. The Renilla and Firefly luciferase gene constructs are obtained from plasmids pGL4.73 and pGL4.13, respectively.

| Plasmid name | Insert gene | Description |
| --- | --- | --- |
| pEP2 | URA3 | 1.1 kbp containing the URA3 gene from yeast is inserted at the unique BamHI site of the vector. |
| pEP1 | URA3 | As pEP2, but with one telomeric repeat shorter by about 100 bp. |

TABLE 3-continued

Description of disclosed plasmids. The Renilla and Firefly luciferase gene constructs are obtained from plasmids pGL4.73 and pGL4.13, respectively.

| Plasmid name | Insert gene | Description |
|---|---|---|
| pEP3 | URA3 | As pEP2, but the orientation of the (T2G4)n-URA3-(C4A2)n cassette is reversed. |
| pEP23 | hRluc (a) | 1.65 kbp containing the Renilla luciferase gene with SV40 promoter, inserted at the unique BamHI site of the vector. Coding region is oriented clockwise. |
| pEP24 | hRluc (b) | 1.65 kbp containing the Renilla luciferase gene with SV40 promoter, inserted at the unique BamHI site of the vector. Coding region is oriented counterclockwise. |
| pEP25 | Luc2 (a) | 2.37 kbp containing the Firefly luciferase gene with SV40 promoter, inserted at the unique BamHI site of the vector. Coding region is oriented clockwise. |
| pEP26 | Luc2 (b) | 2.37 kbp containing the Firefly luciferase gene with SV40 promoter, inserted at the unique BamHI site of the vector. Coding region is oriented counterclockwise. |

These plasmids are part of the Dual-Glo Luciferase Assay System and Vectors, available from Promega (Madison, Wis.).

In one embodiment, the vector is a circular double stranded DNA molecule with sequence comprised of a combination of the following functional sequence elements:

An origin of replication and gene for episomal maintenance in the metazoan host cell. The preferred elements are OriP and the EBNA-1 latency gene from EBV, but it can also comprise other viral elements or combinations with other elements. An example of other viral elements for replication and episomal maintenance are the origin of the Kaposi's sarcoma associated herpesvirus (KSHV) (Hu J., Renne R. 2005 Characterization of the minimal replicator of Kaposi's sarcoma-associated herpesvirus latent origin. J. Virol. 79:2637-42) and the gene for its nuclear antigen 1, LANA-1 (Viejo-Borbolla A., Ottinger M., Bruning E., Burger A., Konig R., Kati E., Sheldon J. A., Schulz T. F. 2005 Brd2/RING3 interacts with a chromatin-binding domain in the Kaposi's Sarcoma-associated herpesvirus latency-associated nuclear antigen 1 (LANA-1) that is required for multiple functions of LANA-1. J. Virol. 79:13618-29). Another example of viral elements for replication and episomal maintenance is the origin of the Bovine papillomavirus (BPV) (Lim D. A., Gossen M., Lehman C. W., Botchan M. R. 1998 Competition for DNA binding sites between the short and long forms of E2 dimers underlies repression in bovine papillomavirus type 1 DNA replication control. J. Virol. 72:1931-40) and the gene for E2 (Lehman C. W., Botchan M. R. 1998 Segregation of viral plasmids depends on tethering to chromosomes and is regulated by phosphorylation. Proc. Natl. Acad. Sci. USA. 95:4338-43).

A selectable marker for expression and growth advantage in a metazoan host cell. The preferred selectable marker is the puromycin-N-acetyl-transferase (PAC) gene, which confers resistance to the antibiotic puromycin, an inhibitor of protein synthesis. Other examples of selectable markers are: hygromycin phosphotransferase B gene (hygromycin resistance); aminoglycoside phosphotransferase II gene (neomycin or G418 resistance); and Zeocin resistance gene, among others. The preferred promoter and polyadenylation signal sequence to direct expression of the selectable marker is the early promoter of SV40 and cognate polyA signal sequence, but other suitable combinations of control elements are possible and available in the field.

An origin of replication and selectable marker for maintenance in a bacterial host cell. The preferred bacterial replicon and selectable marker are ColE1 and the ampicillin resistance gene, respectively. Other suitable elements are well known in the field.

A cloning region with restriction sites for the insertion of other sequences of interest. A single BamHI restriction site is preferred for cloning purposes, but many other sites and combinations of sites are available and well known in the field.

A region of repetitive sequence that is relatively rich in guanine (G). The preferred arrangement for this sequence is as a set of two inverted repeat regions of repetitive DNA flanking the cloning site BamHI, where each repetitive sequence region consists of at least one copy of the 5'-TTGGGG-3' (SEQ ID NO: 1) motif, preferably 33 consecutive copies of the motif, more preferably 50 consecutive copies of the motif, more preferably between 2 and 100 consecutive copies of the motif, without excluding the occurrence of minor mutations in one or more of the motifs such as base substitutions or deletions. Other examples of relatively G-rich sequence motifs that are suitable for a repetitive sequence region include 5'-TTTTGGGG-3' (SEQ ID NO: 2); 5'-TTAGGG-3' (SEQ ID NO: 3); 5'-TGGG-3' (SEQ ID NO: 6); and 5'-TGGTGTACGGA-3' (SEQ ID NO: 14); without excluding combinations of different motifs.

In one embodiment, the vector comprises heterologous polynucleotide cloned into the multiple cloning site of the vector, wherein the heterologous polynucleotide comprises:

A protein coding sequence. The preferred promoter and polyadenylation signal sequence to direct expression of the coding sequence is the early promoter of SV40 and cognate polyA signal sequence, but other suitable combinations of control elements are possible and available in the field, without excluding additional coding motifs or genes singly or in any combination that are intended for the creation of fusion proteins; and/or A genomic DNA sequence containing a gene of interest, where all cognate control elements for expression of the gene are included; and/or A RNA coding sequence, where the transcription product itself is the intended product of interest. Examples of such functional RNA molecules are inhibitory RNA (iRNA), small hairpin RNA (shRNA), among others, and without excluding naturally occurring RNA coding sequences with all cognate elements for transcription and recombinant RNA coding sequences.

Any of a number of standard gene delivery transformation methods can be used with the vectors according to the present invention including lipid mediated transfection (e.g., lipofectamine), receptor mediated transfection, calcium phosphate transfection, electroporation particle bombardment, naked-direct DNA injection, diethylaminoethyl (DEAE-dextran transfection).

The invention also relates to a host cell transformed with the vector according to present invention. The host cell can be from any metazoan organism. For example, cell lines such as HT1080 cells, HeLa cells, CHO cells, K-562 cells, and the like may be used as a host cells.

The invention also relates to a method of producing an RNA molecule comprising contacting a host cell with a vector according to the present invention; and culturing the host cell under suitable culture conditions such that the RNA molecule is transcribed. Host cells are transfected with a vector according to the present invention, followed by selection of transfected cells. The RNA is transcribed from a template in the vector. Such a template is usually a heterologous polynucleotide sequence operably linked to a promoter.

The invention also relates to a method of producing a polypeptide comprising contacting a host cell with the vector according to the present invention, wherein the heterologous polynucleotide sequence encodes the polypeptide; and culturing the host cell under suitable culture conditions such that the polypeptide is expressed. Host cells are transfected with a vector according to the present invention, followed by selection of transfected cells. The RNA is transcribed from a template in the vector. Such a template is usually a heterologous polynucleotide sequence operably linked to a promoter. The polypeptide is translated from the RNA.

EXAMPLES

A transfection method for introducing the Eplus vector into host cells using lipofectamine is described in the legend to Table 4.

and the relatively small episomes, into solution while trapping chromosomal DNA in the insoluble fraction.

Figure 4:
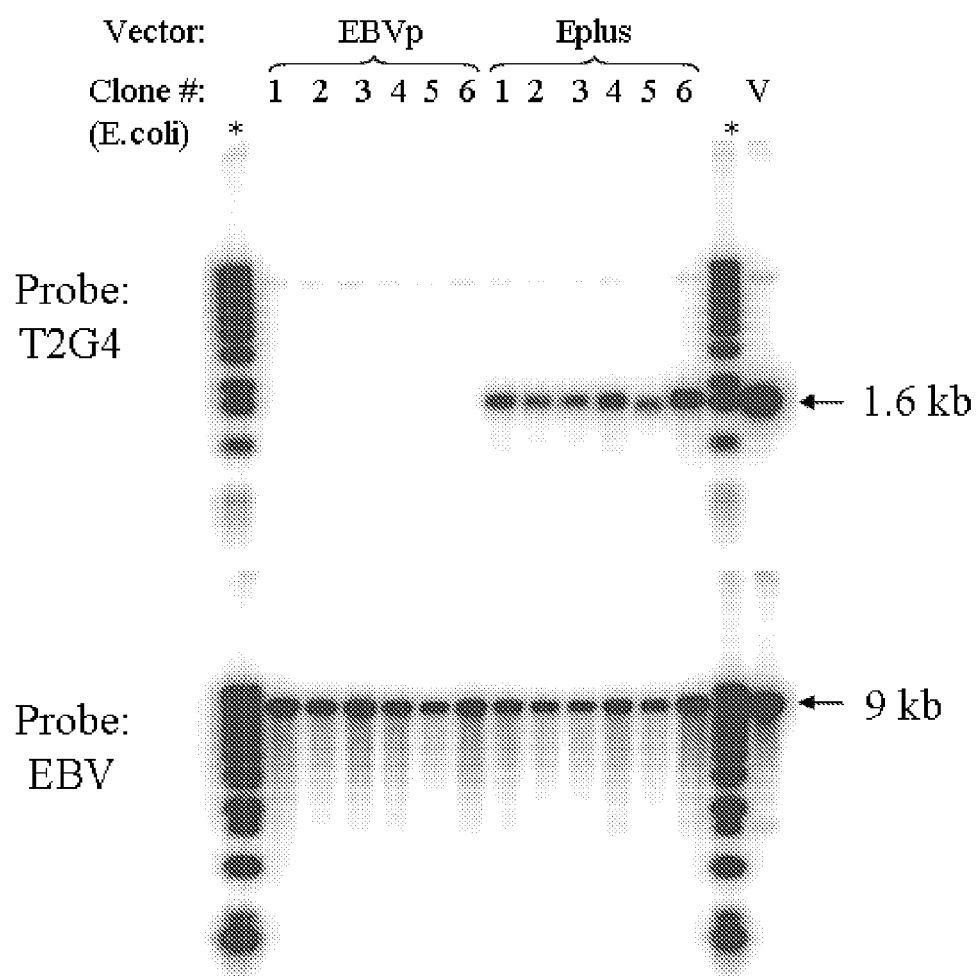
FIG. 4. Southern Blot analysis of plasmids recovered in *E. coli* from stably transfected SV.RNS/HF-1 cells.

FIG. 4 shows Southern blot analysis of plasmids recovered in *E. coli* from stably transfected SV.RNS/HF-1 cells. Cells are transfected with circular episomal control vector (EBVp) or circular Eplus vector. Episomal DNA is extracted from stable puromycin-resistant cells by the method of Hirt. A sample of Hirt extract is then used to transform competent *E. coli*. Six ampicillin-resistant *E. coli* colonies are individually picked and grown for plasmid isolation. Plasmids are digested with XhoI and loaded on a 0.8% agarose gel for electrophoresis along side DNA size markers (*) and Eplus vector (V). A blot of the gel is first probed with a 1.6 kb DNA fragment containing ~700 bp of T2G4 sequence and the URA3 yeast gene (top panel). After striping, the blot is then probed with a 5 kb DNA fragment containing the OriP/EBNA-1 region from EBV (bottom panel). Arrows indicate the fragment size in DNA bands that correspond to the Eplus vector. When samples from the Hirt extracts are used to transform competent *E. coli*, plasmids indistinguishable from the original intact vectors are recovered (FIG. 4).

Moreover, Southern blot analysis of Hirt extracts demonstrates the presence of prototype episomes in cells transfected

TABLE 4

Transfection frequencies of SV40-immortalized human fibroblasts.
Transfection frequency × $10^{-3}$ (No. of Puromycin$^r$ colonies per plate)

| Cell line | Plate No. | Circular EBVp | Linear EBVp (XhoI) | Circular Eplus | Linear Eplus (XhoI) | Linear Eplus (BamHI) |
|---|---|---|---|---|---|---|
| CI39T | 1 | 0.10 (16) | 0.02 (3) | 1.16 (186) | 0.03 (5) | 0.02 (4) |
| | 2 | 0.15 (24) | 0.00 (0) | 1.32 (211) | 0.01 (2) | 0.02 (4) |
| SV/HF-6 | 1 | 0.92 (276) | 0.01 (2) | 2.18 (654) | 0.00 (1) | 0.02 (5) |
| | 2 | 0.79 (236) | 0.00 (0) | 2.14 (643) | 0.01 (4) | 0.01 (3) |
| SV.RNS/HF-1 | 1 | 1.56 (469) | 0.09 (27) | 1.75 (525) | 0.18 (55) | 0.28 (84) |
| | 2 | 1.43 (429) | 0.14 (41) | 1.72 (516) | 0.13 (40) | 0.11 (34) |

Cell lines are transfected with either a circular form or a linearized (restriction-digested) form of an episomal control vector (EBVp) and of the Eplus vector prototype, pEP2. Method: Lipofectamine is used to transfect $1.5 \times 10^6$ cells with 2 μg of vector DNA. Puromycin-resistant transfectants are selected in media containing 0.5 μg puromycin/ml of culture medium. Puromycin-resistant colonies are apparent after 12-15 days in culture. Colonies in two 100 mm plates are fixed with methanol, stained with Giemsa and counted.

As shown in Table 4, the BamHI-digested prototype vector produces stable transfectants at similarly low frequencies as linearized vectors lacking T2G4 repeats altogether: the XhoI-digested control vector (EBVp) and the XhoI-digested prototype (note that digestion of pEP2 with XhoI excises the entire telomeric cassette).

Surprisingly, the intact (i.e. circular) prototype vector produces stable transfectants at significantly higher frequencies than the intact control vector. In the case of the cell line SV.RNS/HF-1, the puromycin-resistant colonies transfected with pEP2 are most likely undercounted. This is because the rapid growth of the transfectants made distinction of individual colonies difficult (see FIG. 3).

Figure 5:
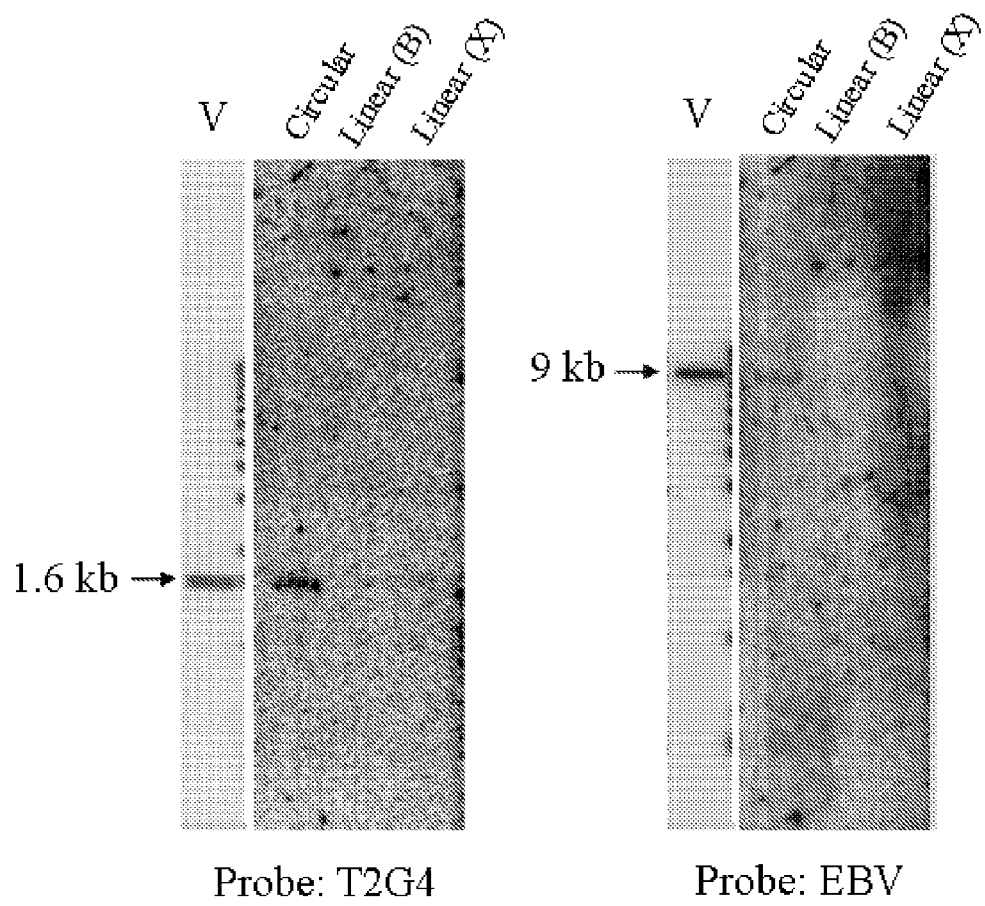
FIG. 5. Southern Blot analysis of Hirt-extracts obtained from stably transfected SV.RNS/HF-1 cells.

To determine if puromycin-resistant cells transfected with intact vectors also maintain them as circular episomes, polyclonal cell populations are extracted by the method of Hirt. (Hirt B. 1967 Selective extraction of polyoma DNA from infected mouse cell cultures. J. Mol. Biol. 26:365-369). This method involves a mild cell lysis that releases the contents of the nucleus and cytoplasm, including mitochondrial DNA with intact pEP2 but not in cells transfected with linearized pEP2 (FIG. 5). FIG. 5 shows Southern blot analysis of Hirt-extracts obtained from stably transfected SV.RNS/HF-1 cells. Cells are transfected with either the circular form or a linearized form of the Eplus vector. Linearization of the vector is carried out by restriction digestion with either BamHI (B) or XhoI (X). Stable puromycin-resistant cells are used to extract episomal DNA by the method of Hirt. Extracts are digested with XhoI and loaded on a 0.8% agarose gel for electrophoresis along side the Eplus vector (V). A blot of the gel is first probed with a 1.6 kb DNA fragment containing ~700 bp of T2G4 sequence and the URA3 yeast gene (left panel). After striping, the blot is then probed with a 5 kb DNA fragment containing the OriP/EBNA-1 region from EBV (right panel). The Vector lane is shown after a shorter exposure than the rest of the blot to account for differences in DNA loading per lane. Arrows indicate the fragment size in DNA bands that correspond to the Eplus vector. These results show that both the prototype vector pEP2 and the control vector EBVp in circular form are replicated and maintained as circular episomes in host cells.

It is concluded T2G4 telomeric repeats, exposed by restriction digestion, are insufficient to support telomere function and stabilize the exposed ends of the linearized episome. However, the T2G4 repeats improve the ability of a circular episomal vector to produce stable transfectants, most likely through a mechanism that is unrelated to telomere formation or function (Brown W., Heller R., Loupart M. L., Shen M. H., Chand A. 1996 Mammalian artificial chromosomes. Curr. Opin. Genet. Dev. 6:281-288).

Careful examination of transfectants also show more vigorous growth of colonies carrying an Eplus vector than controls (see FIG. 3), indicative of higher expression of the selectable marker. Figure shows puromycin resistant colonies of SV.RNS/HF-1 cells transfected with episomal vectors. Puromycin-resistant colonies in 100 mm plates are fixed with methanol and stained with Giemsa.

Figure 6:
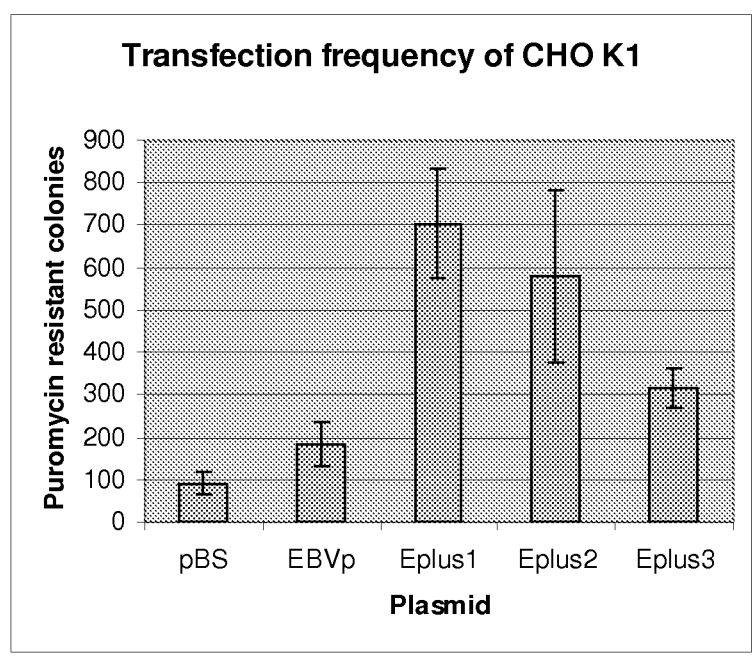
FIG. 6. Transfection frequencies of Chinese Hamster Ovary (CHO) cells.

FIG. 6 shows the results of transfecting CHO cells with a panel of vector plasmids followed by selection for stable transfectants (puromycin resistant colonies). Cells are transfected with either an integrating plasmid (pBS), an episomal control vector (EBVp) or an Eplus plasmid (Eplus1-3). Bars are average number of puromycin resistant colonies per plate (8-9 plates per transfection)+/−standard deviation. Eplus vectors produce higher rates of stable transfectants than a control EBV plasmid (lacking the telomeric repeats) or an integrating plasmid (lacking both EBV elements and telomeric repeats). The stable transfection rates in this cell line are consistent with data using SV40-transformed human fibroblast cell lines which suggest that the Eplus vector is a superior episomal vector design compared to a standard episomal (EBV-based) vector or a conventional integrating vector.

Figure 7:
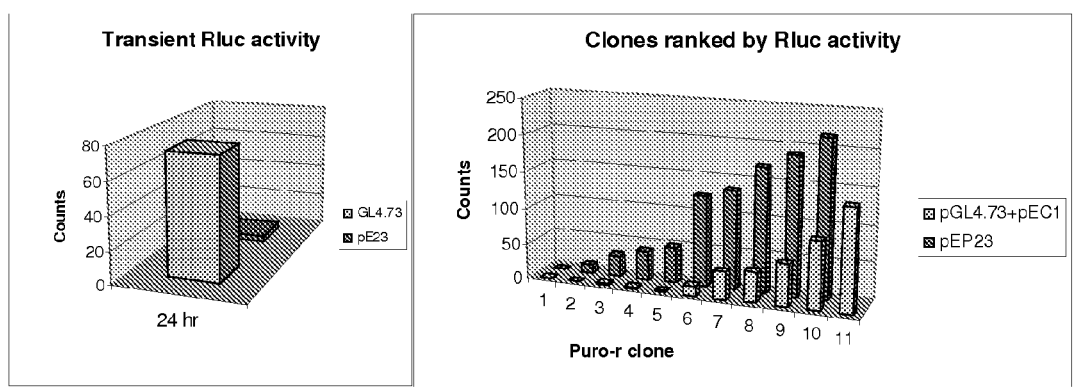
FIG. 7. Luciferase activity in CHO transfectants.

FIG. 7 shows Luciferase activity in CHO transfectants. Left panel: *Renilla* luciferase (hRluc) activity 24 hours post transfection. Cells are transfected with a control plasmid (GL4.73) or and Eplus plasmid (pE23). Right panel: hRluc activity in puromycin resistant clones obtained after ~20 cell divisions. Cells are co-transfected with GL4.73 and an integrating vector carrying the selectable marker (pEC1) or with an Eplus plasmid (pE23). 10 to 11 clones per transfection are selected, expanded and assayed for luciferase activity. Averages from duplicate readings are shown. Clones are ranked by their level of reporter activity.

Transient reporter expression levels are first determined 24 hours post transfection. At this stage, there is higher luciferase activity expressed from a control plasmid than from an Eplus plasmid (FIG. 7). This is partly due to a gene dosage effect, since there are about 5 times more copies of the control plasmid than of the Eplus plasmid per transfection. In contrast, once puromycin resistant clones are selected and expanded for about 20 cell divisions, cells transfected with the Eplus vector showed more than six-fold higher activity on average over controls. These results are consistent with our expectation that Eplus plasmids will naturally attain high copy levels in host cells compared to integrating vectors.

Figure 8:
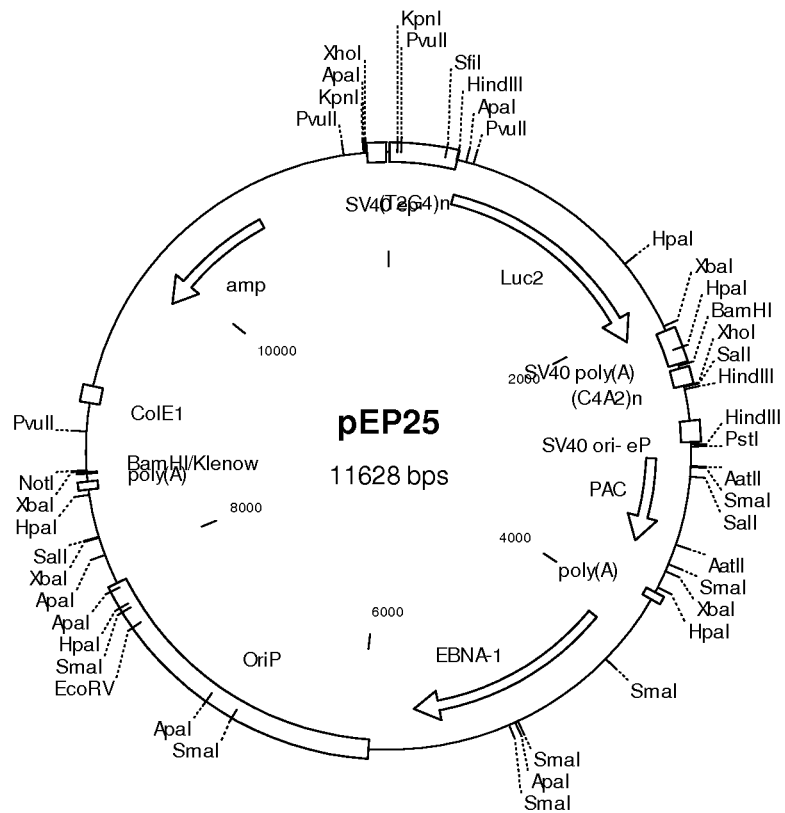
FIG. 8. Map of the prototype Eplus vector, pEP25, which is pEP2 with contains the luciferase gene Luc2 under control of the SV40 promoter.
Figure 9:
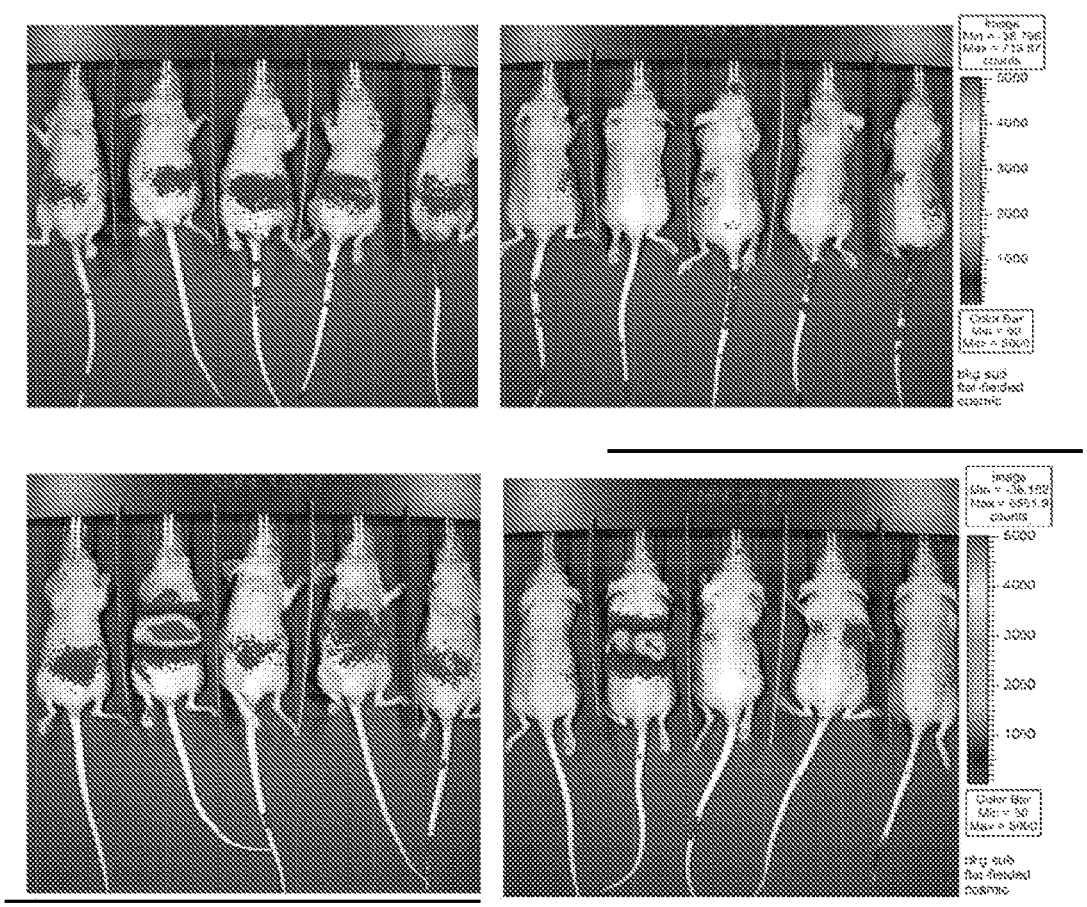
FIG. 9. In vivo transfection and expression of firefly luciferase.

To monitor expression from an Eplus plasmid after in vivo transfection, luciferase activity was assayed in live mice one or two weeks post transfection with either a control vector or an Eplus plasmid (FIG. 8). For this purpose, a commercially available non-viral transfection system was employed (FIG. 9). This particular system targets delivery of vector DNA to the liver. Figure shows in vivo transfection and expression of firefly luciferase using the Eplus plasmid. A total of 10 female athymic nude mice are transfected with either control (pGL4, top panels) or an Eplus plasmid (pEP25, bottom panels) using a commercially available non-viral in vivo transfection kit (TransIT® In Vivo Gene Delivery System from Mirus (Madison, Wis.). One week post transfection, luciferase activity is assayed. Animals are imaged 5-10 min after IP injection of 1 mg luciferin while under anesthesia with 2% isofluorane gas. Imaging is for 5 minutes using medium binning, a field of view of 12.8 or 18.8 cm and an f-stop of 1; an open emission filter is used to maximize the signal. Ventral and Dorsal views are shown (left and right side panels, respectively).

Figure 10:
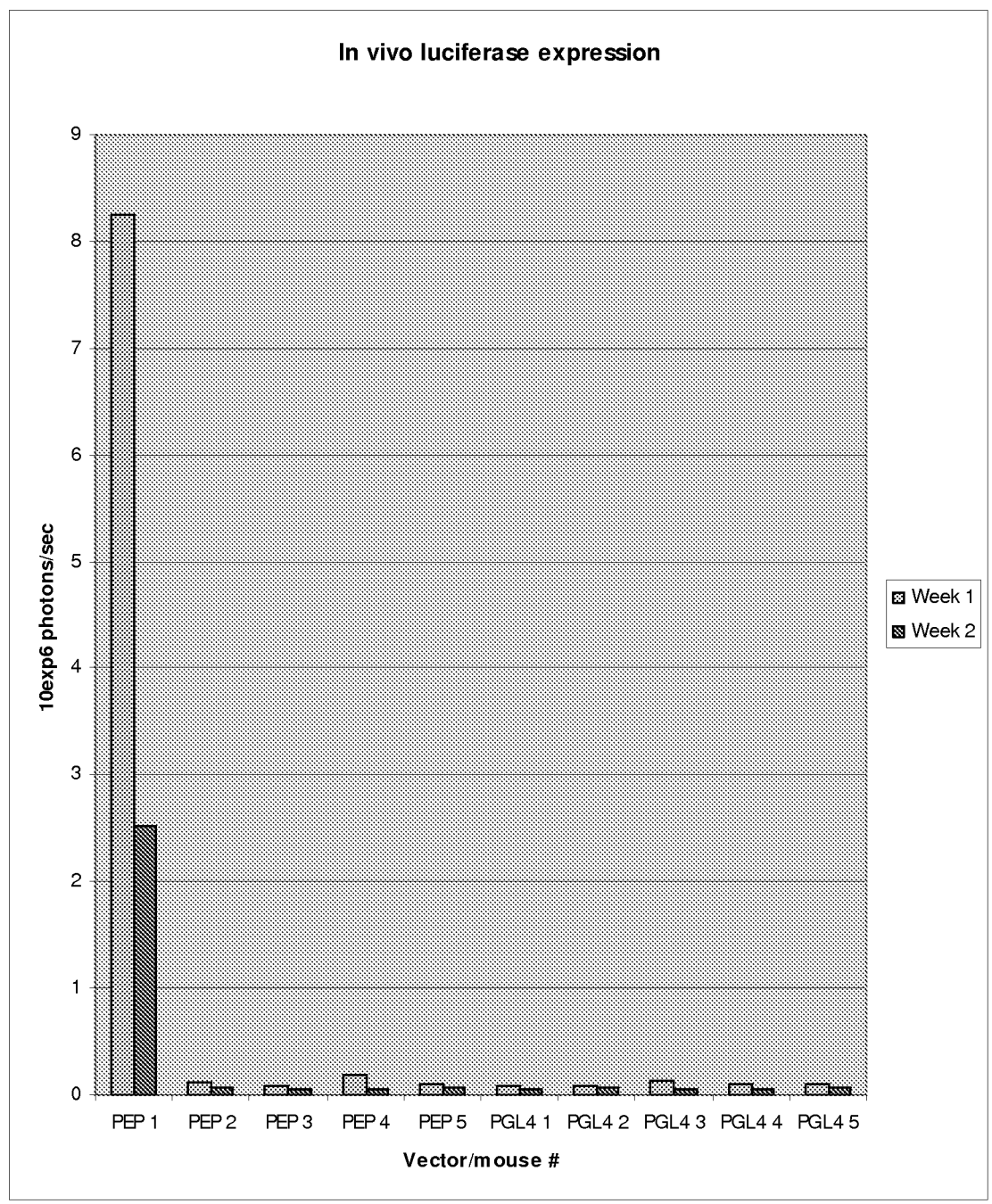
FIG. 10. Quantification of luciferase expression in mice one or two weeks post transfection.
Figure 11:
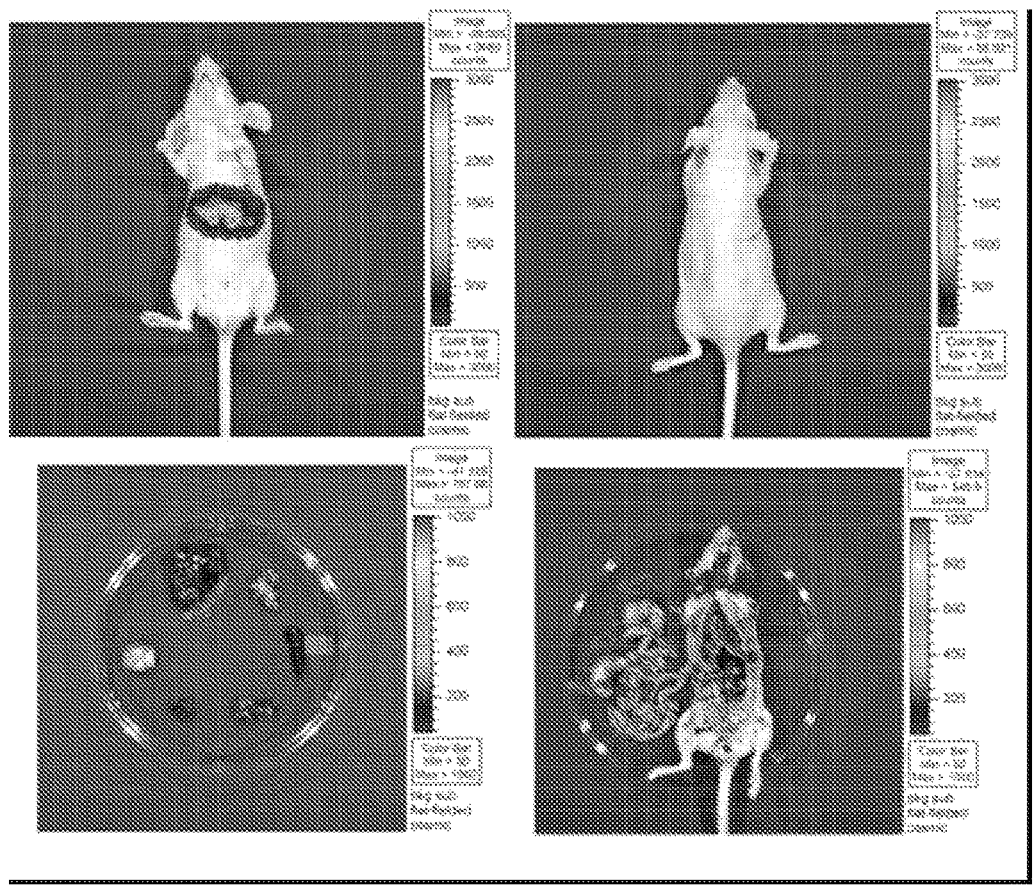
FIG. 11. One of five mice transfected with pEP25 displayed strong expression in the abdominal region two weeks post transfection.

FIG. 10 shows quantification of luciferase expression in mice one or two weeks post transfection. Luciferase activity is determined as described above for FIG. 9. For quantitation, a similar region of interest enclosing the area of the liver is set for each animal and the number of photons/sec emitted from this region is determined using Xenogen's Living Image Software. However, the efficacy of hepatic delivery appears to depend on the rate of DNA injection, which cannot be easily controlled and thus results in considerable variability (FIG. 10). Nevertheless, at least one animal transfected with the Eplus plasmid shows unprecedented levels of luciferase expression in the liver even after two weeks post transfection (FIG. 11), as well as some expression in other regions of the body, suggesting that there are no inherent restrictions to transfection of other target organs or tissues in vivo. One of five mice transfected with pEP25 displays strong expression in the abdominal region two weeks post transfection, as shown in the ventral view (upper left panel; dorsal view is shown in upper right panel). After dissection of the animal, this expression is localized primarily to the liver, with little to no expression in other major organs: lungs, heart, kidney, spleen (lower left panel). However, activity is detected in other parts of the carcass (lower right panel).

All publications cited herein are hereby incorporated by reference.

We claim:

1. A plasmid vector comprising an origin of replication for episomal maintenance in a metazoan cell, a gene for episomal maintenance in said metazoan cell, a polynucleotide sequence comprising a multiple cloning site (MCS), and two inverted repeat regions comprising a telomeric polynucleotide sequence, wherein the two inverted repeat regions are adjacent to the MCS.

2. The vector according to claim 1, wherein said vector comprises a polynucleotide sequence encoding a selectable marker for expression and growth advantage metazoan cell.

3. The vector according to claim 1, wherein said vector further comprises an origin of replication for episomal maintenance in a prokaryotic cell.

4. The vector according to claim 1, wherein said vector comprises a polynucleotide sequence encoding a selectable marker for expression and growth advantage in a prokaryotic cell, said polynucleotide sequence operably linked to a promoter.

5. The vector according to claim 1, wherein said vector comprises a heterologous polynucleotide sequence.

6. The vector according to claim 1, wherein said telomeric polynucleotide sequence is from an organism selected from the group consisting of mammals, Tetrahymena, Euplotes, Oxytricha, Saccharomyces cerevisiae, and Kluyveromyces lactis.

7. The vector according to claim 1, wherein said origin of replication for episomal maintenance in said metazoan cell and said gene for episomal maintenance in said metazoan cell are respectively selected from the group consisting of OriP and EBNA-I latency genes from Epstein-Barr Virus (EBV) origin of the Kaposi's sarcoma associated herpesvirus (KSHV) and the gene for nuclear antigen 1 of KSHV (LANA-I); and origin of the Bovine papillomavirus (BPV) and the gene for E2 from BPV.

8. The vector according to claim 1, wherein said vector comprises a polynucleotide sequence encoding a selectable marker for expression and growth advantage in a metazoan cell wherein said selectable marker for expression and growth advantage in a metazoan cell is selected from the group consisting of puromycin-N-acetyl-transferase (PAC) gene, hygromycin phosphotransferase B gene, aminoglycoside phosphotransferase II gene, and Zeocin resistance gene.

9. The vector according to claim 2 wherein said polynucleotide sequence encoding said selectable marker is operably linked to an early promoter of SV40 and a SV40 polyadenylation signal.

10. The vector according to claim 3, wherein said origin of replication for episomal maintenance in a prokaryotic cell is a bacterial ColE1 origin of replication.

11. The vector according to claim 1, wherein said vector comprises a polynucleotide sequence encoding a selectable marker for expression and growth advantage in a prokaryotic cell, wherein said selectable marker for expression and growth advantage in a prokaryotic cell is selected from the group consisting of ampicillin resistance gene, tetracycline resistance gene, kanamycin resistance gene, chloram-phenicol resistance gene, erythromycin resistance gene, zeocine resistance gene, neomycin resistance gene, hygromycin resistance gene and methotrexate resistance gene.

12. The vector according to claim 1, wherein said telomeric polynucleotide sequence is a region of repetitive sequence that is relatively rich in guanine.

13. The vector according to claim 1, wherein said telomeric polynucleotide sequence is selected from the group consisting of 5'-TTGGGG-3 (SEQ ID NO: 1); 5'-TTTTGGGG-3' (SEQ ID NO: 2); 5'-TTAGGG-3'(SEQ ID NO: 3); 5'-TGGG-3'(SEQ ID NO: 6); and 5'-TGGTGTACGGA-S'(SEQ ID NO: 14).

14. The vector according to claim 1, wherein said vector comprises a heterologous polynucleotide sequence.

15. A vector comprising a polynucleotide sequence consisting of SEQ ID NO: 16.

16. A host cell transformed with the vector according to claim 1.

* * * * *

SEQUENCE LISTING

<160> NUMBER OF SEQ ID NOS: 33

<210> SEQ ID NO 1
<211> LENGTH: 6
<212> TYPE: DNA
<213> ORGANISM: Tetrahymena sp.

<400> SEQUENCE: 1 ttgggg                                                                6

<210> SEQ ID NO 2
<211> LENGTH: 8
<212> TYPE: DNA
<213> ORGANISM: Euplotes sp.

<400> SEQUENCE: 2

-continued

```
ttttgggg                                                        8

<210> SEQ ID NO 3
<211> LENGTH: 6
<212> TYPE: DNA
<213> ORGANISM: Homo sapiens

<400> SEQUENCE: 3 ttaggg                                                          6

<210> SEQ ID NO 4
<211> LENGTH: 2
<212> TYPE: DNA
<213> ORGANISM: Saccharomyces cerevisiae

<400> SEQUENCE: 4 tg                                                              2

<210> SEQ ID NO 5
<211> LENGTH: 3
<212> TYPE: DNA
<213> ORGANISM: Saccharomyces cerevisiae

<400> SEQUENCE: 5 tgg                                                             3

<210> SEQ ID NO 6
<211> LENGTH: 4
<212> TYPE: DNA
<213> ORGANISM: Saccharomyces cerevisiae

<400> SEQUENCE: 6 tggg                                                            4

<210> SEQ ID NO 7
<211> LENGTH: 25
<212> TYPE: DNA
<213> ORGANISM: Kluyveromyces lactis

<400> SEQUENCE: 7
tttgattagg tatgtggtgt acgga                                    25

<210> SEQ ID NO 8
<211> LENGTH: 9
<212> TYPE: RNA
<213> ORGANISM: Tetrahymena americanis

<400> SEQUENCE: 8 caaccccaa                                                       9

<210> SEQ ID NO 9
<211> LENGTH: 15
<212> TYPE: RNA
<213> ORGANISM: Euplotes crassus

<400> SEQUENCE: 9
caaaacccca aaacc                                               15

<210> SEQ ID NO 10
<211> LENGTH: 11
<212> TYPE: RNA
<213> ORGANISM: Homo sapiens

<400> SEQUENCE: 10
```

-continued

```
cuaacccuaa c                                                          11

<210> SEQ ID NO 11
<211> LENGTH: 9
<212> TYPE: RNA
<213> ORGANISM: Mus musculus

<400> SEQUENCE: 11 ccuaacccu                                                              9

<210> SEQ ID NO 12
<211> LENGTH: 16
<212> TYPE: RNA
<213> ORGANISM: Saccharomyces cerevisiae

<400> SEQUENCE: 12
caccacaccc acacac                                                     16

<210> SEQ ID NO 13
<211> LENGTH: 30
<212> TYPE: RNA
<213> ORGANISM: Kluyveromyces lactis

<400> SEQUENCE: 13
ucaaauccgu acaccacaua ccuaaucaaa                                      30

<210> SEQ ID NO 14
<211> LENGTH: 11
<212> TYPE: DNA
<213> ORGANISM: Artificial
<220> FEATURE:
<223> OTHER INFORMATION: telomeric polynucleotide sequence

<400> SEQUENCE: 14
tggtgtacgg a                                                          11

<210> SEQ ID NO 15
<211> LENGTH: 18
<212> TYPE: DNA
<213> ORGANISM: Artificial
<220> FEATURE:
<223> OTHER INFORMATION: synthetic inverted repeat ("IR") sequence
      example
<220> FEATURE:
<221> NAME/KEY: misc_feature
<222> LOCATION: (7)..(12)
<223> OTHER INFORMATION: n is a, c, g, or t

<400> SEQUENCE: 15
ttggggnnnn nnccccaa                                                   18

<210> SEQ ID NO 16
<211> LENGTH: 10454
<212> TYPE: DNA
<213> ORGANISM: Artificial
<220> FEATURE:
<223> OTHER INFORMATION: prototype Eplus vector (pEP2)

<400> SEQUENCE: 16
ttgttccagt ttggaacaag agtccactat taaagaacgt ggactccaac gtcaaagggc     60
gaaaaaccgt ctatcagggc gatggcccac tacgtgaacc atcaccctaa tcaagttttt    120
tggggtcgag gtgccgtaaa gcactaaatc ggaaccctaa agggagcccc cgatttagag    180
cttgacgggg aaagccggcg aacgtggcga gaaaggaagg gaagaaagcg aaaggagcgg    240
gcgctagggc gctggcaagt gtagcggtca cgctgcgcgt aaccaccaca cccgccgcgc    300
```

```
ttaatgcgcc gctacagggc gcgtcccatt cgccattcag gctgcgcaac tgttgggaag      360
ggcgatcggt gcgggcctct tcgctattac gccagctggc gaaaggggga tgtgctgcaa      420
ggcgattaag ttgggtaacg ccagggtttt cccagtcacg acgttgtaaa acgacggcca      480
gtgaattgta atacgactca ctatagggcg aattgggtac cgggccccccc ctcgaggggg      540
gttggggttg gggttggggt tggggttggg gttggggttg gggttggggt tggggttggg      600
gttggggttg gggttggggt tggggttggg gttggggttg gggttggggt tgggtctgc       660
ctcgcgcgga tcccgggtaa taactgatat aattaaattg aagctctaat ttgtgagttt      720
agtatacatg catttactta taatacagtt ttttagtttt gctggccgaa tcttctcaaa      780
tatgcttccc agcctgcttt tctgtaacgt tcaccctcta ccttagcatc cgttcctttt      840
gcaaatagtc ctcttccaac aataataatg tcagatcctg tagagaccac atcatccacg      900
gttctatact gttgacccaa tgcgtctccc ttgtcatcta aacccacacc gggtgtcata      960
atcaaccaat cgtaaccttc atctcttcca cccatgtctc tttgagcaat aaagccgata     1020
acaaaatctt tgtcgctctt cgcaatgtca acagtaccct tagtatattc tccagtagat     1080
agggagccct tgcatgacaa ttctgctaac atcaaaaggc ctctaggttc ctttgttact     1140
tcttctgccg cctgcttcaa accgctaaca atacctgggc ccaccacacc gtgtgcattc     1200
gtaatgtctg cccattctgc tattctgtat acacccgcag agtactgcaa tttgactgta     1260
ttaccaatgt cagcaaattt tctgtcttcg aagagtaaaa aattgtactt ggcggataat     1320
gcctttagcg gcttaactgt gccctccatg gaaaaatcag tcaagatatc cacatgtgtt     1380
tttagtaaac aaattttggg acctaatgct tcaactaact ccagtaattc cttggtggta     1440
cgaacatcca atgaagcaca caagtttgtt tgcttttcgt gcatgatatt aaatagcttg     1500
gcagcaacag gactaggatg agtagcagca cgttccttat atgtagcttt cgacatgatt     1560
tatcttcgtt tcctgcaggt ttttgttctg tgcagttggg ttaagaatac tgggcaattt     1620
catgttctt caacactaca tatgcgtata tataccaatc taagtctgtg ctccttcctt     1680
cgttcttcct tctgttcgga gattaccgaa tcaaaaaaat ttcaaggaaa ccgaaatcaa     1740
aaaaagaat aaaaaaaaa tgatgaattg aaaagctcca ttccttgcgg cggcggtgct     1800
caacggcctc aacctactac tgggctgctt cctaatgcag gagtcgcata agggagagcg     1860
tcgagggat ccgcgcgagg cagacccccaa ccccaaccc aaccccctcc caaacccac     1920
caaaacccaa ccaaccccca accaaacttt ttctcccaac cccaaccca accccaaccc     1980
caaccccaac cccctcgag gtcgacggta tcgataagct tgatctgtgg aatgtgtgtc     2040
agttagggtg tggaaagtcc ccaggctccc cagcaggcag aagtatgcaa agcatgcatc     2100
tcaattagtc agcaaccagg tgtggaaagt ccccaggctc cccagcaggc agaagtatgc     2160
aaagcatgca tctcaattag tcagcaacca tagtcccgcc cctaactccg cccatcccgc     2220
ccctaactcc gcccagttcc gcccattctc cgccccatgg ctgactaatt tttttatt     2280
atgcagaggc cgaggccgcg gcctctgagc tattccagaa gtagtgagga ggcttttttg     2340
gaggcctagg cttttgcaaa aagcttgcat gcctgcaggt cggccgccac gaccggtgcc     2400
gccaccatcc cctgacccac gcccctgacc cctcacaagg agacgacctt ccatgaccga     2460
gtacaagccc acggtgcgcc tcgccacccg cgacgacgtc ccccgggccg tacgcaccct     2520
cgccgccgcg ttcgccgact accccgccac gcgccacacc gtcgacccgg accgccacat     2580
cgagcgggtc accgagctgc aagaactctt cctcacgcgc gtcgggctcg acatcggcaa     2640
ggtgtgggtc gcggacgacg gcgccgcggt ggcggtctgg accacgccgg agagcgtcga     2700
```

```
agcggggycg gtgttcgccg agatcggccc gcgcatggcc gagttgagcg gttcccggct    2760
ggccgcgcag caacagatgg aaggcctcct ggcgccgcac cggcccaagg agcccgcgtg    2820
gttcctggcc accgtcggcg tctcgcccga ccaccagggc aagggtctgg gcagcgccgt    2880
cgtgctcccc ggagtggagg cggccgagcg cgccggggtg cccgccttcc tggagacctc    2940
cgcgccccgc aacctcccct tctacgagcg gctcggcttc accgtcaccg ccgacgtcga    3000
ggtgcccgaa ggaccgcgca cctggtgcat gacccgcaag cccggtgcct gacgcccgcc    3060
ccacgacccg cagcgcccga ccgaaaggag cgcacgaccc catggctccg accgaagcca    3120
cccggggcgg ccccgccgac cccgcacccg ccccccgaggc ccaccgactc tagaggatca    3180
taatcagcca taccacattt gtagaggttt tacttgcttt aaaaaacctc ccacacctcc    3240
ccctgaacct gaaacataaa atgaatgcaa ttgttgttgt taacttgttt attgcagctt    3300
ataatggtta caaataaagc aatagcatca caaatttcac aaataaagca ttttttttcac   3360 tgcattctag ttgtggtttg tccaaactca tcaatgtatc ttatcatgtc tgcctggctt    3420
gaggctcagg acgcaaatct tgaggatgtt cagcgggagt tttccgggct gcgagtaatt    3480
ggtgatgagg acgaggatgg ttcggaggat ggggaatttt cagacctgga tctgtctgac    3540
agcgaccatg aaggggatga gggtgggggg gctgttggag ggggcaggag tctgcactcc    3600
ctgtattcac tgagcgtcgt ctaataaaga tgtctattga tctcttttag tgtgaatcat    3660
gtctgacgag gggccaggta caggacctgg aaatggccta ggagagaagg gagacacatc    3720
tggaccagaa ggctccggcg gcagtggacc tcaaagaaga gggggtgata accatggacg    3780
aggacgggga agaggacgag gacgaggagg cggaagacca ggagcccgg gcggctcagg    3840 atcaggcca agacatagag atggtgtccg gagacccaa aaacgtccaa gttgcattgg    3900
ctgcaaaggg acccacggtg gaacaggagc aggagcagga gcgggagggg caggaggggc    3960
aggagcagga ggggcaggag gggcaggagc aggaggggca ggaggggcag gaggaggagg    4020
aggggcagga ggggcaggag caggaggagg ggcaggaggg gcaggagcag gaggggcagg    4080
aggggcagga gcaggagggg caggagggc aggagcagga gggcaggag gggcaggagc    4140 aggaggaggg gcaggagcag gaggggcagg agcaggaggt ggaggccggg gtcgaggagg    4200
cagtggaggc cggggtcgag gaggtagtgg aggccgggt cgaggaggta gtggaggccg    4260
ccggggtaga ggacgtgaaa gagccagggg gggaagtcgt gaaagagcca ggggagagg    4320 tcgtggacgt ggagaaaaga ggcccaggag tcccagtagt cagtcatcat catccgggtc    4380
tccaccgcgc aggccccctc caggtagaag gccattttc caccctgtag gggaagccga    4440
ttattttgaa taccaccaag aaggtggccc agatggtgag cctgacgtgc ccccgggagc    4500
gatagagcag ggccccgcag atgacccagg agaaggccca agcactggac cccggggtca    4560
gggtgatgga ggcaggcgca aaaaggagg gtggtttgga aagcatcgtg gtcaaggagg    4620
ttccaacccg aaatttgaga acattgcaga aggtttaaga gctctcctgg ctaggagtca    4680
cgtagaaagg actaccgacg aaggaacttg ggtcgccggt gtgttcgtat atggaggtag    4740
taagacctcc ctttacaacc taaggcgagg aactgcccct gctattccac aatgtcgtct    4800
tacaccattg agtcgtctcc cctttggaat ggccctgga cccggccac aacctggccc    4860 gctaagggag tccattgtct gttatttcat ggtcttttta caaactcata tatttgctga    4920
ggttttgaag gatgcgatta aggaccttgt tatgacaaag cccgctccta cctgcaatat    4980
cagggtgact gtgtgcagct ttgacgatgg agtagattg cctccctggt ttccacctat    5040
ggtggaaggg gctgccgcgg agggtgatga cggagatgac ggagatgaag gaggtgatgg    5100
```

```
agatgagggt gaggaagggc aggagtgatg taacttgtta ggagacgccc tcaatcgtat    5160
taaaagccgt gtattccccc gcactaaaga ataaatcccc agtagacatc atgcgtgctg    5220
ttggtgtatt tctggccatc tgtcttgtca ccattttcgt cctcccaaca tgggcaatt     5280 gggcataccc atgttgtcac gtcactcagc tccgcgctca acaccttctc gcgttggaaa    5340
acattagcga catttacctg gtgagcaatc agacatgcga cggctttagc ctggcctcct    5400
taaattcacc taagaatggg agcaaccagc aggaaaagga caagcagcga aaattcacgc    5460
cccttgggga ggtggcggca tatgcaaagg atagcactcc cactctacta ctgggtatca    5520
tatgctgact gtatatgcat gaggatagca tatgctaccc ggatatagat taggatagca    5580
tatactaccc agatatagat taggatagca tatgctaccc agatatagat taggatagcc    5640
tatgctaccc agatataaat taggatagca tatactaccc agatatagat taggatagca    5700
tatgctaccc agatatagat taggatagcc tatgctaccc agatatagat taggatagca    5760
tatgctaccc agatatagat taggatagca tatgctatcc agatatttgg gtagtatatg    5820
ctacccagat ataaattagg atagcatata ctaccctaat ctctattagg atagcatatg    5880
ctacccggat acagattagg atagcatata ctacccagat atagattagg atagcatatg    5940
ctacccagat atagattagg atagcctatg ctacccagat ataaattagg atagcatata    6000
ctacccagat atagattagg atagcatatg ctacccagat atagattagg atagcctatg    6060
ctacccagat atagattagg atagcatatg ctatccagat atttgggtag tatatgctac    6120
ccatggcaac attagcccac cgtgctctca gcgacctcgt gaatatgagg accaacaacc    6180
ctgtgcttgg cgctcaggcg caagtgtgtg taatttgtcc tccagatcgc agcaatcgcg    6240
cccctatctt ggcccgccca cctacttatg caggtattcc ccggggtgcc attagtggtt    6300
ttgtgggcaa gtggtttgac cgcagtggtt agcggggtta caatcagcca agttattaca    6360
cccttatttt acagtccaaa accgcagggc ggcgtgtggg ggctgacgcg tgccccccact    6420 ccacaatttc aaaaaaaaga gtggccactt gtctttgttt atgggcccca ttggcgtgga    6480
gccccgttta atttcggggg tgttagagac aaccagtgg agtccgctgc tgtcggcgtc    6540
cactctcttt cccttgtta caaatagagt gtaacaacat ggttcacctg tcttggtccc    6600
tgcctgggac acatcttaat aaccccagta tcatattgca ctaggattat gtgttgccca    6660
tagccataaa ttcgtgtgag atggacatcc agtctttacg gcttgtcccc accccatgga    6720
tttctattgt taaagatatt cagaatgttt cattcctaca ctagtattta ttgcccaagg    6780
ggtttgtgag ggttatattg gtgtcatagc acaatgccac cactgaaccc cccgtccaaa    6840
ttttattctg ggggcgtcac ctgaaaacctt gttttcgagc acctcacata caccttactg    6900
ttcacaactc agcagttatt ctattagcta aacgaaggag aatgaagaag caggcgaaga    6960
ttcaggagag ttcactgccc gctccttgat cttcagccac tgcccttgtg actaaaatgg    7020
ttcactaccc tcgtggaatc ctgaccccat gtaaataaaa ccgtgacagc tcatggggtg    7080
ggagatatcg ctgttcctta ggaccctttt actaacccta attcgatagc atatgcttcc    7140
cgttgggtaa catatgctat tgaattaggg ttagtctgga tagtatatac tactacccgg    7200
gaagcatatg ctaccgtttt agggttaaca aggggccctt ataaacacta ttgctaatgc    7260
cctcttgagg gtccgcttat cggtagctac acaggcccct ctgattgacg ttggtgtagc    7320
ctcccgtagt cttcctgggc ccctgggagg tacatgtccc ccagcattgg tgtaagagct    7380
tcagccaaga gttacacata aaggcaatgt tgtgttgcag tccacagact gcaaagtctg    7440
ctccaggatg aaagccactc agtgttggca aatgtgcaca tccatttata aggatgtcaa    7500
```

```
ctacagtcag agaacccctt tgtgtttggt ccccccccgt gtcacatgtg aacagggcc    7560 cagttggcaa gttgtaccaa ccaactgaag ggattacatg cactgccccg cgaagaaggg   7620
gcagagatgt cgtagtcagg tttagttcgt ccggggcggg gatcgatcct ctagagtcga   7680
cctcatggct gcgccccgac acccgccaac acccgctgac gcgccctgac gggcttgtct   7740
gctcccggca tccgcttaca gacaagctgt gaccgtctcc gggagctgca tgtgtcagag   7800
gttttcaccg tcatcaccga aacgcgcgag gcagccggat cataatcagc cataccacat   7860
ttgtagaggt tttacttgct ttaaaaaacc tcccacacct cccctgaac ctgaaacata    7920 aaatgaatgc aattgttgtt gttaacttgt ttattgcagc ttataatggt tacaaataaa   7980
gcaatagcat cacaaatttc acaaataaag cattttttc actgcattct agttgtggtt    8040
tgtccaaact catcaatgta tcttatcatg tctggatcga tccactagtt ctagagcggc   8100
cgccaccgcg gtggagctcc agcttttgtt ccctttagtg agggttaatt tcgagcttgg   8160
cgtaatcatg gtcatagctg tttcctgtgt gaaattgtta tccgctcaca attccacaca   8220
acatacgagc cggaagcata aagtgtaaag cctggggtgc ctaatgagtg agctaactca   8280
cattaattgc gttgcgctca ctgcccgctt tccagtcggg aaacctgtcg tgccagctgc   8340
attaatgaat cggccaacgc gcggggagag gcggtttgcg tattgggcgc tcttccgctt   8400
cctcgctcac tgactcgctg cgctcggtcg ttcggctgcg gcgagcggta tcagctcact   8460
caaaggcggt aatacggtta tccacagaat caggggataa cgcaggaaag aacatgtgag   8520
caaaaggcca gcaaaaggcc aggaaccgta aaaaggccgc gttgctggcg ttttccata    8580 ggctccgccc ccctgacgag catcacaaaa atcgacgctc aagtcagagg tggcgaaacc   8640
cgacaggact ataaagatac caggcgtttc cccctggaag ctccctcgtg cgctctcctg   8700
ttccgaccct gccgcttacc ggatacctgt ccgcctttct cccttcggga agcgtggcgc   8760
tttctcatag ctcacgctgt aggtatctca gttcggtgta ggtcgttcgc tccaagctgg   8820
gctgtgtgca cgaacccccc gttcagcccg accgctgcgc cttatccggt aactatcgtc   8880
ttgagtccaa cccggtaaga cacgacttat cgccactggc agcagccact ggtaacagga   8940
ttagcagagc gaggtatgta ggcggtgcta cagagttctt gaagtggtgg cctaactacg   9000
gctacactag aagaacagta tttggtatct gcgctctgct gaagccagtt accttcggaa   9060
aaagagttgg tagctcttga tccggcaaac aaaccaccgc tggtagcggt ggtttttttg   9120
tttgcaagca gcagattacg cgcagaaaaa aaggatctca agaagatcct ttgatctttt   9180
ctacggggtc tgacgctcag tggaacgaaa actcacgtta agggattttg gtcatgagat   9240
tatcaaaaag gatcttcacc tagatccttt taaattaaaa atgaagtttt aaatcaatct   9300
aaagtatata tgagtaaact tggtctgaca gttaccaatg cttaatcagt gaggcaccta   9360
tctcagcgat ctgtctattt cgttcatcca tagttgcctg actccccgtc gtgtagataa   9420
ctacgatacg ggagggctta ccatctggcc ccagtgctgc aatgataccg cgagacccac   9480
gctcaccggc tccagattta tcagcaataa accagccagc cggaagggcc gagcgcagaa   9540
gtggtcctgc aactttatcc gcctccatcc agtctattaa ttgttgccgg gaagctagag   9600
taagtagttc gccagttaat agtttgcgca acgttgttgc cattgctaca ggcatcgtgg   9660
tgtcacgctc gtcgtttggt atggcttcat tcagctccgg ttcccaacga tcaaggcgag   9720
ttacatgatc ccccatgttg tgcaaaaaag cggttagctc cttcggtcct ccgatcgttg   9780
tcagaagtaa gttggccgca gtgttatcac tcatggttat ggcagcactg cataattctc   9840
ttactgtcat gccatccgta agatgctttt ctgtgactgg tgagtactca accaagtcat   9900
```

```
tctgagaata gtgtatgcgg cgaccgagtt gctcttgccc ggcgtcaata cgggataata    9960
ccgcgccaca tagcagaact ttaaaagtgc tcatcattgg aaaacgttct tcggggcgaa   10020
aactctcaag gatcttaccg ctgttgagat ccagttcgat gtaacccact cgtgcaccca   10080
actgatcttc agcatctttt actttcacca gcgtttctgg gtgaggataa acaggaaggc   10140
aaaatgccgc aaaaaaggga ataagggcga cacggaaatg ttgaatactc atactcttcc   10200
tttttcaata ttattgaagc atttatcagg gttattgtct catgagcgga tacatatttg   10260
aatgtattta gaaaaataaa caaatagggg ttccgcgcac atttccccga aaagtgccac   10320
ctaaattgta agcgttaata ttttgttaaa attcgcgtta aatttttgtt aaatcagctc   10380
attttttaac caataggccg aaatcggcaa aatcccttat aaatcaaaag aatagaccga   10440
gatagggttg agtg                                                    10454
```

<210> SEQ ID NO 17
<211> LENGTH: 9
<212> TYPE: DNA
<213> ORGANISM: Dictyostelium sp.
<220> FEATURE:
<221> NAME/KEY: repeat_unit
<222> LOCATION: (2)..(9)
<223> OTHER INFORMATION: g can be shown 1-8 times

<400> SEQUENCE: 17 aggggggggg                                                              9

<210> SEQ ID NO 18
<211> LENGTH: 6
<212> TYPE: DNA
<213> ORGANISM: Paramecium sp.

<400> SEQUENCE: 18 ttgggk                                                                  6

<210> SEQ ID NO 19
<211> LENGTH: 7
<212> TYPE: DNA
<213> ORGANISM: Plasmodium sp.

<400> SEQUENCE: 19 ttagggy                                                                 7

<210> SEQ ID NO 20
<211> LENGTH: 7
<212> TYPE: DNA
<213> ORGANISM: Arabidopsis thaliana

<400> SEQUENCE: 20 tttaggg                                                                 7

<210> SEQ ID NO 21
<211> LENGTH: 8
<212> TYPE: DNA
<213> ORGANISM: Chlamydomonas sp.

<400> SEQUENCE: 21 ttttaggg                                                                8

<210> SEQ ID NO 22
<211> LENGTH: 5
<212> TYPE: DNA
<213> ORGANISM: Bombyx mori

-continued

<400> SEQUENCE: 22 ttagg                                                              5

<210> SEQ ID NO 23
<211> LENGTH: 6
<212> TYPE: DNA
<213> ORGANISM: Ascaris lumbricoides

<400> SEQUENCE: 23 ttaggc                                                             6

<210> SEQ ID NO 24
<211> LENGTH: 14
<212> TYPE: DNA
<213> ORGANISM: Schizosaccharomyces pombe
<220> FEATURE:
<221> NAME/KEY: repeat_region
<222> LOCATION: (3)..(6)
<223> OTHER INFORMATION: one or both of a and c may be repeated once
<220> FEATURE:
<221> NAME/KEY: repeat_unit
<222> LOCATION: (7)..(14)
<223> OTHER INFORMATION: g may be shown 1-8 times

<400> SEQUENCE: 24
ttacacgggg gggg                                                   14

<210> SEQ ID NO 25
<211> LENGTH: 13
<212> TYPE: DNA
<213> ORGANISM: Saccharomyces cerevisiae

<400> SEQUENCE: 25
tgtgggtgtg gtg                                                    13

<210> SEQ ID NO 26
<211> LENGTH: 16
<212> TYPE: DNA
<213> ORGANISM: Saccharomyces cerevisiae
<220> FEATURE:
<221> NAME/KEY: repeat_unit
<222> LOCATION: (1)..(3)
<223> OTHER INFORMATION: g can be shown 2-3 times
<220> FEATURE:
<221> NAME/KEY: repeat_unit
<222> LOCATION: (4)..(15)
<223> OTHER INFORMATION: tg can be shown 1-6 times

<400> SEQUENCE: 26
gggtgtgtgt gtgtgt                                                 16

<210> SEQ ID NO 27
<211> LENGTH: 15
<212> TYPE: DNA
<213> ORGANISM: Candida glabrata

<400> SEQUENCE: 27
ggggtctggg tgctg                                                  15

<210> SEQ ID NO 28
<211> LENGTH: 23
<212> TYPE: DNA
<213> ORGANISM: Candida albicans

<400> SEQUENCE: 28
ggtgtacgga tgtctaactt ctt                                         23

```
<210> SEQ ID NO 29
<211> LENGTH: 23
<212> TYPE: DNA
<213> ORGANISM: Candida tropicalis

<400> SEQUENCE: 29
ggtgtamgga tgtcacgatc att                                            23

<210> SEQ ID NO 30
<211> LENGTH: 23
<212> TYPE: DNA
<213> ORGANISM: Candida maltosa

<400> SEQUENCE: 30
ggtgtacgga tgcagactcg ctt                                            23

<210> SEQ ID NO 31
<211> LENGTH: 7
<212> TYPE: DNA
<213> ORGANISM: Candida guillermondii

<400> SEQUENCE: 31 ggtgtac                                                               7

<210> SEQ ID NO 32
<211> LENGTH: 25
<212> TYPE: DNA
<213> ORGANISM: Kluyveromyces lactis

<400> SEQUENCE: 32
ggtgtacgga tttgattagg tatgt                                          25

<210> SEQ ID NO 33
<211> LENGTH: 25
<212> TYPE: DNA
<213> ORGANISM: Candida pseudotropicalis

<400> SEQUENCE: 33
ggtgtacgga tttgattagt tatgt                                          25
```